(12) United States Patent
Bonanomi et al.

(10) Patent No.: US 7,799,815 B2
(45) Date of Patent: Sep. 21, 2010

(54) TRIAZOLE DERIVATIVES AS MODULATORS OF DOPAMINE D3 RECEPTORS

(75) Inventors: Giorgio Bonanomi, Verona (IT); Romano Di Fabio, Verona (IT); Elettra Fazzolari, Verona (IT); Dieter Hamprecht, Verona (IT); Fabrizio Micheli, Verona (IT); Luca Tarsi, Verona (IT); Silvia Terreni, Verona (IT)

(73) Assignee: Glaxo Group Limited, Middlesex (GB)

( * ) Notice: Subject to any disclaimer, the term of this patent is extended or adjusted under 35 U.S.C. 154(b) by 87 days.

(21) Appl. No.: 12/064,128

(22) PCT Filed: Aug. 18, 2006

(86) PCT No.: PCT/EP2006/008200

§ 371 (c)(1),
(2), (4) Date: Aug. 13, 2008

(87) PCT Pub. No.: WO2007/022933

PCT Pub. Date: Mar. 1, 2007

(65) Prior Publication Data

US 2009/0221593 A1    Sep. 3, 2009

(30) Foreign Application Priority Data

Aug. 22, 2005  (GB) .................................. 0517181.4
Aug. 22, 2005  (GB) .................................. 0517202.8

(51) Int. Cl.
A01N 43/64    (2006.01)
A61K 31/41    (2006.01)
C07D 249/08   (2006.01)
C07D 249/00   (2006.01)
C07D 249/12   (2006.01)

(52) U.S. Cl. ...................... 514/383; 514/384; 548/262.2; 548/262.4; 548/263.2; 548/264.2

(58) Field of Classification Search .................. 514/383, 514/384; 548/262.2, 262.4, 263.2, 264.2
See application file for complete search history.

(56) References Cited

U.S. PATENT DOCUMENTS

| 2007/0142438 | A1 | 6/2007  | Arista et al. ................. 514/341 |
| 2007/0249642 | A1 | 10/2007 | Bertani et al. ............... 514/269 |
| 2008/0058398 | A1 | 3/2008  | Anderton et al. ............ 514/374 |
| 2008/0167357 | A1 | 7/2008  | Hamprecht et al. ......... 514/384 |
| 2008/0176917 | A1 | 7/2008  | Andreotti et al. ............ 514/384 |
| 2008/0227837 | A1 | 9/2008  | Arista et al. ................. 514/384 |
| 2008/0242715 | A1 | 10/2008 | Capelli et al. ............... 514/384 |
| 2009/0030062 | A1 | 1/2009  | Gentile et al. ............... 514/412 |
| 2009/0036461 | A1 | 2/2009  | Hamprecht et al. .... 514/252.06 |
| 2009/0124629 | A1 | 5/2009  | Bonanomi et al. ..... 514/252.06 |
| 2009/0221618 | A1 | 9/2009  | Arista et al. ................. 514/274 |

FOREIGN PATENT DOCUMENTS

WO    WO00/42036       7/2000
WO    WO2004/031181    4/2004
WO    WO2004/069830    8/2004
WO    WO2005/080382   9/2005
WO    WO2006/108701   10/2006

OTHER PUBLICATIONS

U.S. Appl. No. 11/917,352, filed Jun. 13, 2006, Arista, et al.
U.S. Appl. No. 12/295,024, filed Mar. 30, 2007, Bertani, et al.
U.S. Appl. No. 12/295,304, filed Mar. 30, 2007, Bertani, et al.

*Primary Examiner*—Sreeni Padmanabhan
*Assistant Examiner*—Sarah Pihonak
(74) *Attorney, Agent, or Firm*—James M. Kanagy; Edward R. Gimmi; Charles M. Kinzig

(57) ABSTRACT

The present invention relates to novel compounds of formula (I) or a salt thereof:

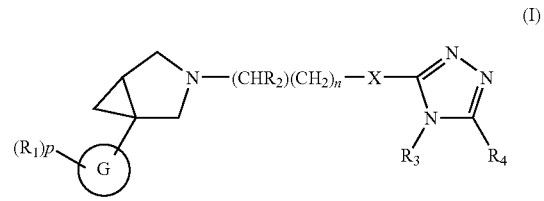

(I)

wherein:
G is a 5- or 6-membered heteroaromatic group, or is a 9- or 10-membered bicyclic heteroaromatic group containing one or two heteroatoms independently selected from nitrogen and oxygen, wherein G is not pyridyl, indazolyl or benzothiazolyl;
p is an integer ranging from 0 to 4;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl or $SF_5$; or corresponds to a group $R_5$;
$R_2$ is hydrogen or $C_{1-4}$alkyl;
n is 2 or 3;
X is S or —$CH_2$—;
$R_3$ is $C_{1-4}$alkyl;
$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy and $C_{1-4}$alkanoyl;
$R_5$ is isoxazolyl, —$CH_2$—N-pyrrolyl, 1,1-dioxido-2-isothiazolidinyl, thienyl, thiazolyl, pyridyl or 2-pyrrolidinonyl, wherein each group is optionally substituted by one or two substituents selected from: halogen, cyano, $C_{1-4}$alkyl, halo$C_{1-4}$alkyl, $C_{1-4}$alkoxy and $C_{1-4}$alkanoyl;
processes for their preparation, intermediates used in these processes, pharmaceutical compositions containing them and their use in therapy, as modulators of dopamine $D_3$ receptors, e.g. to treat substance related disorders, as antipsychotic agents, premature ejaculation or cognition impairment.

15 Claims, No Drawings

TRIAZOLE DERIVATIVES AS MODULATORS OF DOPAMINE D3 RECEPTORS

The present invention relates to novel compounds, processes for their preparation, intermediates used in these processes, pharmaceutical compositions containing them and their use in therapy, as modulators of dopamine $D_3$ receptors.

WO 2002/40471 (SmithKline Beecham) discloses certain benzazepine compounds having activity at the dopamine $D_3$ receptor.

Recently a patent application has been published as WO2005/080382 and discloses the following compounds of formula (I) or a salt thereof:

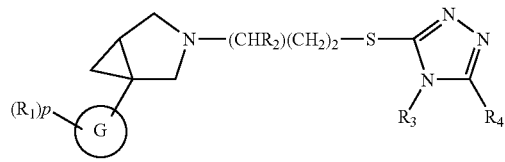

(I)

wherein
G is selected from a group consisting of: phenyl, pyridyl, benzothiazolyl, indazolyl;
p is an integer ranging from 0 to 5;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl; or corresponds to a group $R_5$;
$R_2$ is hydrogen or $C_{1-4}$alkyl;
$R_3$ is $C_{1-4}$alkyl;
$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl;
$R_5$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;

and when $R_1$ is chlorine and p is 1, such $R_1$ is not present in the ortho position with respect to the linking bond to the rest of the molecule; and when $R_1$ corresponds to $R_5$, p is 1.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

The present invention provides a compound of formula (I) or a salt thereof:

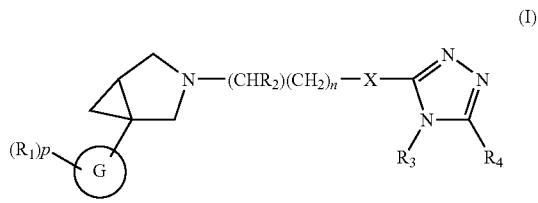

(I)

wherein:

G is a 5- or 6-membered heteroaromatic group, or is a 9- or 10-membered bicyclic heteroaromatic group containing one or two heteroatoms independently selected from nitrogen and oxygen, wherein G is not pyridyl, indazolyl or benzothiazolyl;

p is an integer ranging from 0 to 4;

$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl or $SF_5$; or corresponds to a group $R_5$;

$R_2$ is hydrogen or $C_{1-4}$alkyl;

n is 2 or 3;

X is S or —$CH_2$—;

$R_3$ is $C_{1-4}$alkyl;

$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy and $C_{1-4}$alkanoyl;

$R_5$ is isoxazolyl, —$CH_2$—N-pyrrolyl, 1,1-dioxido-2-isothiazolidinyl, thienyl, thiazolyl, pyridyl or 2-pyrrolidinonyl, wherein each group is optionally substituted by one or two substituents selected from: halogen, cyano, $C_{1-4}$alkyl, halo$C_{1-4}$alkyl, $C_{1-4}$alkoxy and $C_{1-4}$alkanoyl.

The term "5- or 6-membered heteroaromatic group" refers to a non-saturated carbocyclic ring wherein one, two or three of the carbon atoms are replaced by nitrogen, sulfur and/or oxygen. Examples include pyrrolyl, pyrrolinyl, pyrazolinyl, imidazolyl, pyrazolyl, oxazolyl, isoxazolyl, oxadiazolyl, isothiazolyl, thiazolyl, furyl, thienyl, thiadiazolyl, triazolyl, thiazinyl, triazinyl, pyridazinyl, pyrimidinyl and pyrazinyl.

The term "9- or 10-membered bicyclic heteroaromatic group containing one or two heteroatoms independently selected from nitrogen and oxygen" refers to a 9-membered or a 10-membered bicyclic fused aromatic ring containing one or two heteroatoms independently selected from nitrogen and oxygen. Examples include indolyl, benzimidazolyl, benzofuranyl, benzothiophenyl, benzoxazoly, quinolinyl, isoquinolinyl, cinnolinyl, phthalazinyl, quinazolinyl and quinoxalinyl.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "n-$C_{1-4}$alkyl" refers to the unbranched alkyls as defined above.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "$C_{1-4}$alkanoyl" refers to an alkanoyl group having from 1 to 4 carbon atoms, such as methanoyl (or "formyl"), ethanoyl (or "acetyl"), propanoyl, isopropanoyl, butanoyl, isobutanoyl and sec-butanoyl.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

The term "5- or 6-membered heteroaromatic group" refers to a monocyclic 5- or 6-membered heterocyclic group containing 1, 2, 3 or 4 heteroatoms, for example from 1 to 3 heteroatoms, selected from O, N and S. When the group contains 2-4 heteroatoms, one may be selected from O, N and S and the remaining heteroatoms may be N. Examples of 5 and 6-membered heteroaromatic groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "8- to 11-membered bicyclic group" refers to a bicyclic ring system containing a total of 8, 9, 10 or 11 carbon atoms, wherein 1, 2, 3 or 4 or 5 of the carbon atoms are optionally replaced by a heteroatom independently selected from O, S and N. The term includes bicyclic systems wherein both rings are aromatic, as well as bicyclic ring systems wherein one of the rings is partially or fully saturated. Examples of 8- to 11-membered bicyclic groups wherein both rings are aromatic include indenyl, naphthyl and azulenyl. Examples of 8- to 11-membered bicyclic groups having 1, 2, 3, 4 or 5 heteroatoms, in which both rings are aromatic, include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl. Examples of 8- to 11-membered bicyclic groups having 1, 2, 3, 4 or 5 heteroatoms, in which one of the rings is partially or fully saturated includes dihydrobenzofuranyl, indanyl, tetrahydronaphthyl, indolinyl, isoindolinyl, tetrahydroisoquinolinyl, tetrahydroquinolyl, benzoxazinyl and benzoazepinyl.

The term "heterocyclyl" refers to a 5 or 6-membered monocyclic or 8 to 11-membered bicyclic group wherein 1, 2, 3, 4 or 5 of the carbon atoms are replaced by a heteroatom independently selected from O, S and N and which is partially or fully saturated. Examples of "heterocyclyl" which are fully saturated 5 or 6-membered monocyclic rings include pyrrolidinyl, imidazolidinyl, pyrazolidinyl, isothiazolyl, thiazolyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl. Examples of "heterocyclyl" groups which are partially saturated 5 or 6-membered monocyclic rings include oxazolinyl, isoxazolinyl, imidazolinyl, pyrazolinyl, 1,2,3,6-tetrahydropyridyl and 3,6-dihydro-2H-pyranyl. Examples of "heterocyclyl" groups which are fully saturated 8 to 11-membered bicyclic rings include decahydroquinolinyl, octahydro-2H-1,4-benzoxazinyl and octahydro-1H-cyclopenta-[b]pyridinyl. Examples of "heterocyclyl" groups which are partially saturated 8 to 11-membered bicyclic rings include 2,3-dihydro-1H-indolyl, 1,2,3,4-tetrahydroquinolinyl, 1,2,3,4-tetrahydroisoquinolinyl and 2,3,4,5-tetrahydro-1H-3-benzazepinyl.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

In one embodiment, G is a 5- or 6-membered heteroaromatic group containing one or two heteroatoms independently selected from nitrogen and oxygen, which is not pyridyl.

In one embodiment, G is furanyl, pyrrolyl, pyrrolinyl, pyrrolidinyl, oxazolyl, imidazolyl, pyrazolidinyl, isoxazolyl, pyranyl, pyridinyl, pyridazinyl, pyrimidinyl, thienyl or pyrazinyl.

In another embodiment G is pyrimidinyl.

In one embodiment, G is a 9- or 10-membered bicyclic heteroaromatic group containing one or two heteroatoms independently selected from nitrogen and oxygen, which is not indazolyl or benzothiazolyl. In one embodiment, G is indolyl, benzimidazolyl, benzofuranyl, benzothiophenyl, benzoxazoly, quinolinyl, isoquinolinyl, cinnolinyl, phthalazinyl, quinazolinyl or quinoxalinyl. For example, G is quinolinyl or benzoxazolyl.

In another embodiment G is quinolinyl or benzoxazolyl.

In one embodiment, $R_1$ is $C_{1-4}$alkyl.

In one embodiment, $R_2$ is hydrogen.

In one embodiment p is 0 or 1.

In one embodiment n is 2.

In one embodiment, $R_5$ is a group selected from: isoxazolyl, 2-pyrrolidinonyl, 1,1-dioxido-2-isothiazolidinyl which is optionally substituted by one or two substituents selected from: halogen, cyano, $C_{1-2}$alkyl (e.g. methyl), halo$C_{1-2}$alkyl (e.g. trifluoromethyl), $C_{1-2}$alkoxy (e.g. methoxy) and $C_{1-3}$alkanoyl (e.g. acetyl). For example, $R_5$ is isoxazolyl, 2-pyrrolidinonyl, —$CH_2$—N-pyrrolyl, 1,1-dioxido-2-isothiazolidinyl, 2-thienyl, 2-pyridyl or 2-thiazolyl.

In one embodiment, p is 1 or 2.

In another embodiment p is 0.

In one embodiment X is —S—.

In one embodiment, R₄ is optionally substituted phenyl (e.g. phenyl, 4-trifluoromethyl-phenyl, 3,4-difluorophenyl), an optionally substituted bicyclic group such as quinolinyl (e.g. 2-methylquinoline, 8-fluoro-2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl (e.g. 5-chloro-1-methyl-1H-pyrazol-4-yl, 1-methyl-3-trifluoromethyl-1H-pyrazol-4-yl 1,5-dimethyl-1H-pyrazoly-4-yl), an optionally substituted pyrimidyl (e.g. 5-pyrimidinyl), an optionally substituted pyridazinyl (e.g. 4-pyridazinyl), an optionally substituted pyrazinyl (e.g. 5-methyl-2-pyrazinyl), an optionally substituted furanyl (e.g. 3-methyl-2-furanyl, 2,5-dimethyl-3-furanyl), an optionally substituted thienyl (e.g. 5-chloro-2-thienyl), an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

Because of the presence of the fused cyclopropane, compounds of formula (I) are believed to have a "cis" disposition of the substituents (both groups linked to the bicyclic ring system are on the same face of this bicyclic ring system). In another embodiment of the present invention compounds of formula (I)' are provided which correspond to the compounds of formula (I) having "cis" disposition, represented by the bold highlight of the bonds:

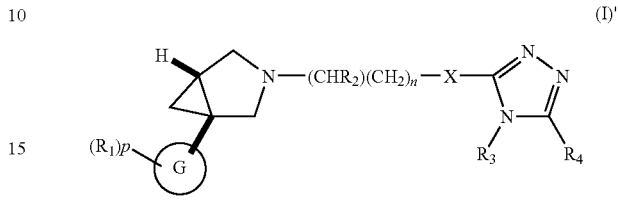

(I)' wherein G, p, R₁, R₂, R₃ and R₄ are defined as above for compounds of formula (I).

The two configurations of compounds of formula (I)' are shown below:

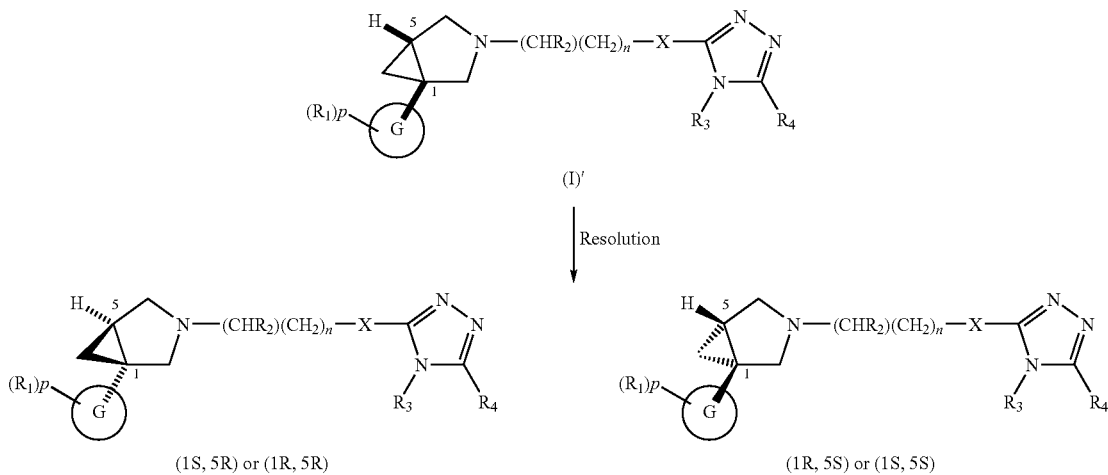

In another embodiment R₄ is optionally substituted phenyl (e.g. phenyl, 4-trifluoromethyl-phenyl, 3,4-difluorophenyl) or optionally substituted oxazolyl (e.g. 4-methyl-1,3-oxazol-5-yl, 2-methyl-5-trifluoromethyl-1,3-oxazol-4-yl).

In one embodiment, R₃ is methyl.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

It will be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

the configuration of sterechemical center named 1 may change due to Cahn-Ingold-Prelog nomenclature priorities, depending on G meaning.

In a further embodiment of the present invention compounds of formula (IA) are provided that correspond to stereochemical isomers of compounds of formula (I)', enriched in configuration (1S,5R) or (1R,5R):

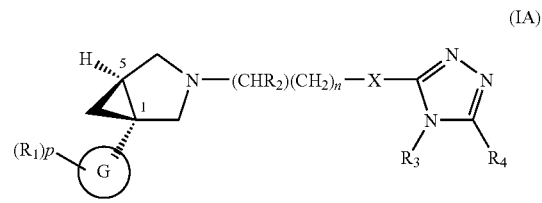

(IA)

wherein G, p, X, n, R₁, R₂, R₃, R₄, and R₅ are defined as above for compounds of formula (I)' or a salt thereof.

In a further embodiment of the present invention compounds of formula (IB) are provided that correspond to stereochemical isomers of compounds of formula (I)', enriched in configuration (1R,5S) or (1S,5S):

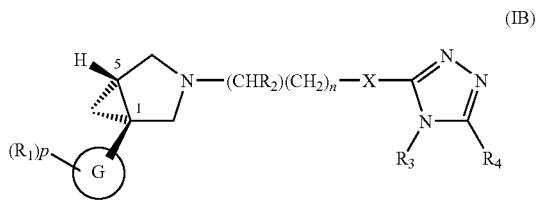

(IB)

wherein G, p, X, n, $R_1$, $R_2$, $R_3$, $R_4$, and $R_5$ are defined as above for compounds of formula (I)' or a salt thereof.

It is intended in the context of the present invention that stereochemical isomers enriched in configuration (1S,5R) or (1R,5R) of formula (IA) correspond in one embodiment to at least 90% e.e. In another embodiment the isomers correspond to at least 95% e.e. In another embodiment the isomers correspond to at least 99% e.e.

It is intended in the context of the present invention that stereochemical isomers enriched in configuration (1R,5S) or (1S,5S) of formula (IB) correspond in one embodiment to at least 90% e.e. In another embodiment the isomers correspond to at least 95% e.e. In another embodiment the isomers correspond to at least 99% e.e.

In another embodiment, a compound of formula (IC) or a salt thereof is provided, wherein $R_1$, p, $R_3$ and $R_4$ are as defined for formula (I):

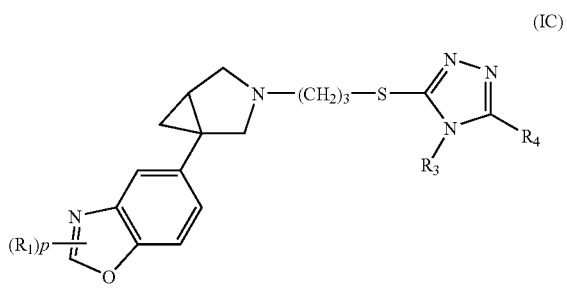

(IC)

In Formula (IC), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy and $C_{1-4}$alkanoyl. Examples of $R_4$ include optionally substituted phenyl (e.g. phenyl, 4-trifluoromethyl-phenyl, 3,4-difluorophenyl), an optionally substituted bicyclic group such as quinolinyl (e.g. 2-methylquinoline, 8-fluoro-2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl (e.g. 5-chloro-1-methyl-1H-pyrazol-4-yl, 1-methyl-3-trifluoromethyl-1H-pyrazol-4-yl 1,5-dimethyl-1H-pyrazoly-4-yl), an optionally substituted pyrimidyl (e.g. 5-pyrimidinyl), an optionally substituted pyridazinyl (e.g. 4-pyridazinyl), an optionally substituted pyrazinyl (e.g. 5-methyl-2-pyrazinyl), an optionally substituted furanyl (e.g. 3-methyl-2-furanyl, 2,5-dimethyl-3-furanyl), an optionally substituted thienyl (e.g. 5-chloro-2-thienyl), an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

In one embodiment, for compounds of formula (IC), p is 1 and $R_1$ is $C_{1-4}$alkyl (for example ethyl).

In another embodiment, a compound of formula (ID) or a salt thereof is provided, wherein $R_1$, p, $R_3$ and $R_4$ are as defined for formula (I):

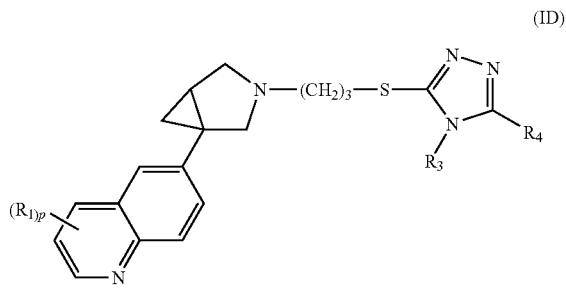

(ID)

In Formula (ID), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy and $C_{1-4}$alkanoyl. Examples of $R_4$ include those defined previously for compounds (IC).

In one embodiment, for compounds of formula (ID), p is 1 and $R_1$ is $C_{1-4}$alkyl (for example methyl).

In another embodiment, for compounds of formula (ID), p is 0.

In another embodiment, a compound of formula (ID)' or a salt thereof is provided, wherein $R_1$, p, $R_3$ and $R_4$ are as defined for formula (I):

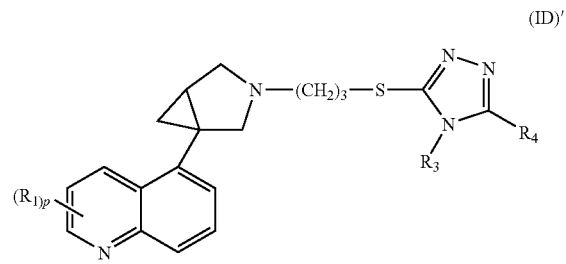

(ID)'

In Formula (ID)', in one embodiment, $R_3$ is methyl, $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy and $C_{1-4}$alkanoyl. Examples of $R_4$ include those defined previously for compounds (IC).

In one embodiment, for compounds of formula (ID)', p is 1 and $R_1$ is hydrogen.

In another embodiment, for compounds of formula (ID)', p is 0.

In another embodiment, a compound of formula (IE) or a salt thereof is provided, wherein $R_1$, p, $R_3$ and $R_4$ are as defined for formula (I):

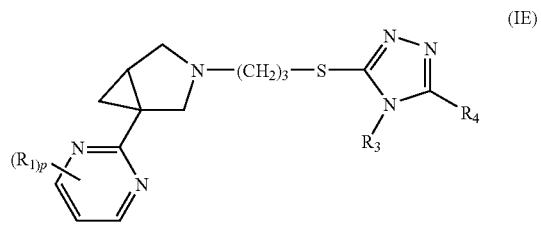

(IE)

In Formula (IE), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy and $C_{1-4}$alkanoyl. Examples of $R_4$ include those defined previously for compounds (IC).

In one embodiment, for compounds of formula (IE), p is 0.

In a further embodiment of the present invention compounds of formula (IF) are provided that correspond to stereochemical isomers of compounds of formula (IC), enriched in configuration (1S,5R):

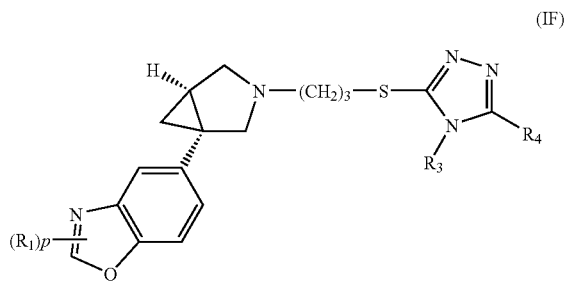

(IF)

wherein $R_1$, $R_2$, $R_3$, and $R_4$ are defined as above for compounds of formula (I) or a salt thereof.

In a further embodiment of the present invention compounds of formula (IG) are provided that correspond to stereochemical isomers of compounds of formula (IC), enriched in configuration (1R,5S):

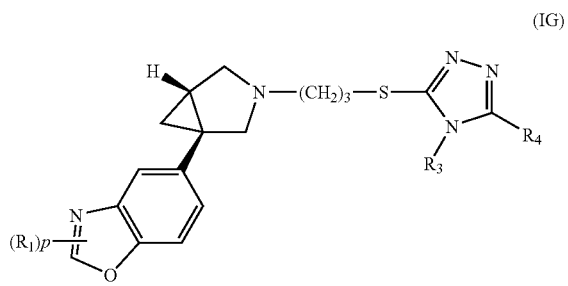

(IG)

wherein $R_1$, $R_2$, $R_3$, and $R_4$ are defined as above for compounds of formula (I) or a salt thereof.

In a further embodiment of the present invention compounds of formula (IH) are provided that correspond to stereochemical isomers of compounds of formula (ID), enriched in configuration (1S,5R):

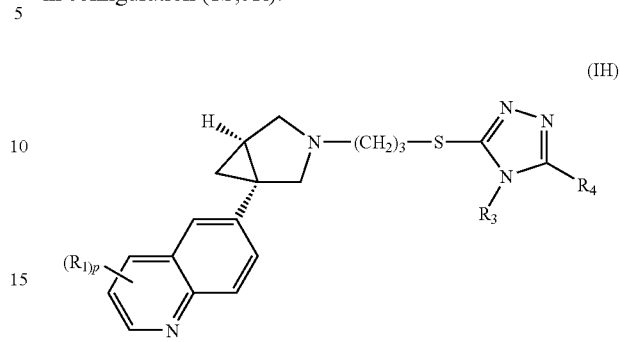

(IH)

wherein $R_1$, $R_2$, $R_3$, and $R_4$ are defined as above for compounds of formula (I) or a salt thereof.

In a further embodiment of the present invention compounds of formula (IH)' are provided that correspond to stereochemical isomers of compounds of formula (ID)', enriched in configuration (1S,5R):

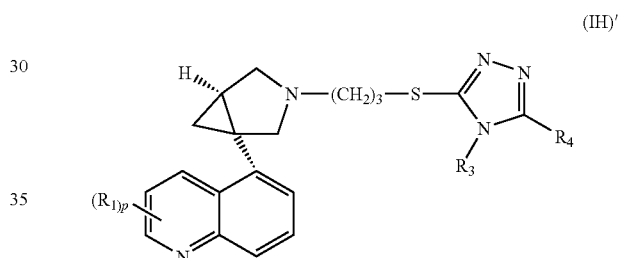

(IH)' wherein $R_1$, $R_2$, $R_3$, and $R_4$ are defined as above for compounds of formula (I) or a salt thereof.

In a further embodiment of the present invention compounds of formula (IL) are provided that correspond to stereochemical isomers of compounds of formula (ID), enriched in configuration (1R,5S):

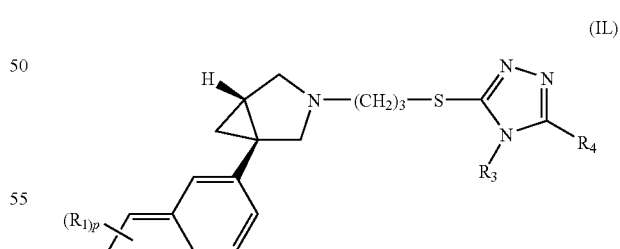

(IL)

wherein $R_1$, $R_2$, $R_3$, and $R_4$ are defined as above for compounds of formula (I) or a salt thereof.

In a further embodiment of the present invention compounds of formula (IL)' are provided that correspond to stereochemical isomers of compounds of formula (ID)', enriched in configuration (1R,5S):

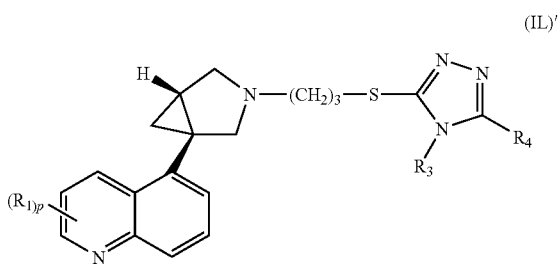

(IL)' wherein $R_1$, $R_2$, $R_3$, and $R_4$ are defined as above for compounds of formula (I) or a salt thereof.

In a further embodiment of the present invention compounds of formula (IM) are provided that correspond to stereochemical isomers of compounds of formula (IE), enriched in configuration (1R,5R):

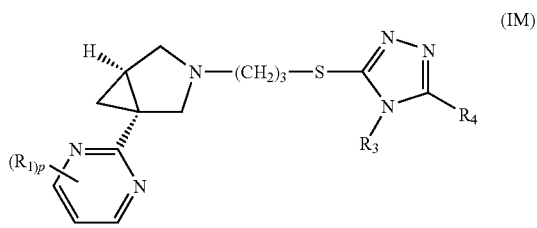

(IM)

wherein $R_1$, $R_2$, $R_3$, and $R_4$ are defined as above for compounds of formula (I) or a salt thereof.

In a further embodiment of the present invention compounds of formula (IN) are provided that correspond to stereochemical isomers of compounds of formula (IE), enriched in configuration (1S,5S):

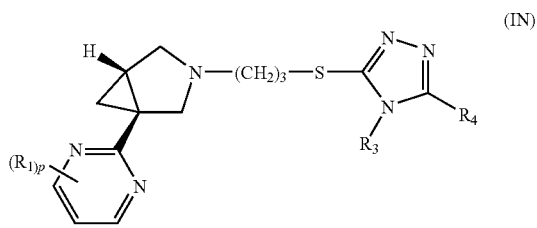

(IN)

wherein $R_1$, $R_2$, $R_3$, and $R_4$ are defined as above for compounds of formula (I) or a salt thereof.

Certain of the compounds of the invention may form acid addition salts with less than one equivalent, or one or more equivalents of the acid. The present invention includes within its scope all possible stoichiometric and non-stoichiometric forms.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

In one embodiment of the present invention compounds are provided e a molecular weight of 800 or less. In another embodiment compounds are provided having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Example compounds of the present invention include:
2-methyl-6-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]quinoline;
2-ethyl-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzoxazole;
(1R,5S/1S,5R)-6-[3-(3-{[4-methyl-5-(4-methyl-1,3-oxazol-5-yl)-4H-1,2,4-triazol-3-yl]thio}-propyl)-3-azabicyclo[3.1.0]hex-1-yl]quinoxaline;
(1R,5S/1S,5R)-3-(3-{[4-methyl-5-(4-methyl-1,3-oxazol-5-yl)-4H-1,2,4-triazol-3-yl]thio}propyl)-1-(2-methyl-5-pyrimidinyl)-3-azabicyclo[3.1.0]hexane;
(1S,5S/1R,5R)-3-(3-{[4-methyl-5-(4-methyl-1,3-oxazol-5-yl)-4H-1,2,4-triazol-3-yl]thio}propyl)-1-(5-methyl-2-thienyl)-3-azabicyclo[3.1.0]hexane;
5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]quinoline;
(1S,5S/1R,5R)-3-(3-{[4-methyl-5-(4-methyl-1,3-oxazol-5-yl)-4H-1,2,4-triazol-3-yl]thio}propyl)-1-(2-pyrimidinyl)-3-azabicyclo[3.1.0]hexane;
(1S,5S/1R,5R)-3-(3-{[5-(3,4-difluorophenyl)-4-methyl-4H-1,2,4-triazol-3-yl]thio}propyl)-1-(2-pyrimidinyl)-3-azabicyclo[3.1.0]hexane;

and salts thereof.

The present invention also provides a process for preparing a compound of formula (I) or a salt thereof as defined above, which process comprises reacting a compound of formula (II):

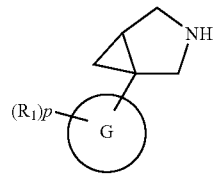

(II)

wherein $R_1$, p and G are as defined for formula (I), with a compound of formula (III):

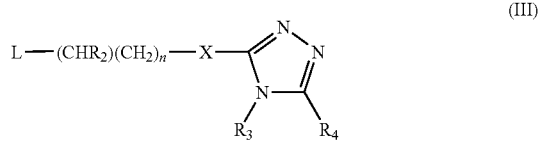

(III)

wherein X, n, $R_2$, $R_3$ and $R_4$ are as defined for formula (I) and L is a leaving group, and thereafter optionally:

(i) removing any protecting group(s); and/or (ii) forming a salt; and/or (iii) converting a compound of formula (I) or a salt thereof to another compound of formula (I) or a salt thereof.

The above process may be performed using conventional methods for the formation of a tertiary amine. The leaving group L may be a halogen such as chlorine. Alternatively L may be a sulfonyloxy group such $C_{1-4}$alkylsulfonyloxy (e.g. methanesulfonyloxy), $C_{1-4}$alkylsulfonyloxy or halo$C_{1-4}$ alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When L is a halogen the reaction may be carried out using a base such as potassium carbonate in the presence of a source of iodide such as sodium iodide in a solvent such as N,N-dimethylformamide at a suitable temperature, e.g. 60° C.

Compounds of formula (II) may be prepared by methods well known in the art (e.g. J. Med. Chem. 1981, 24, 481-490; and Adv. Synth. Catal. 2001, 343 (3), 299). Interconversion of groups R₁ may be effected by methodology well known in the art (e.g. demethylation of a methoxy group resulting in a hydroxy group using a suitable Lewis acidic reagent such as boron tribromide in an inert solvent such as dichloromethane).

One general route which may be used for the preparation of a compound of formula (II) is as follows:

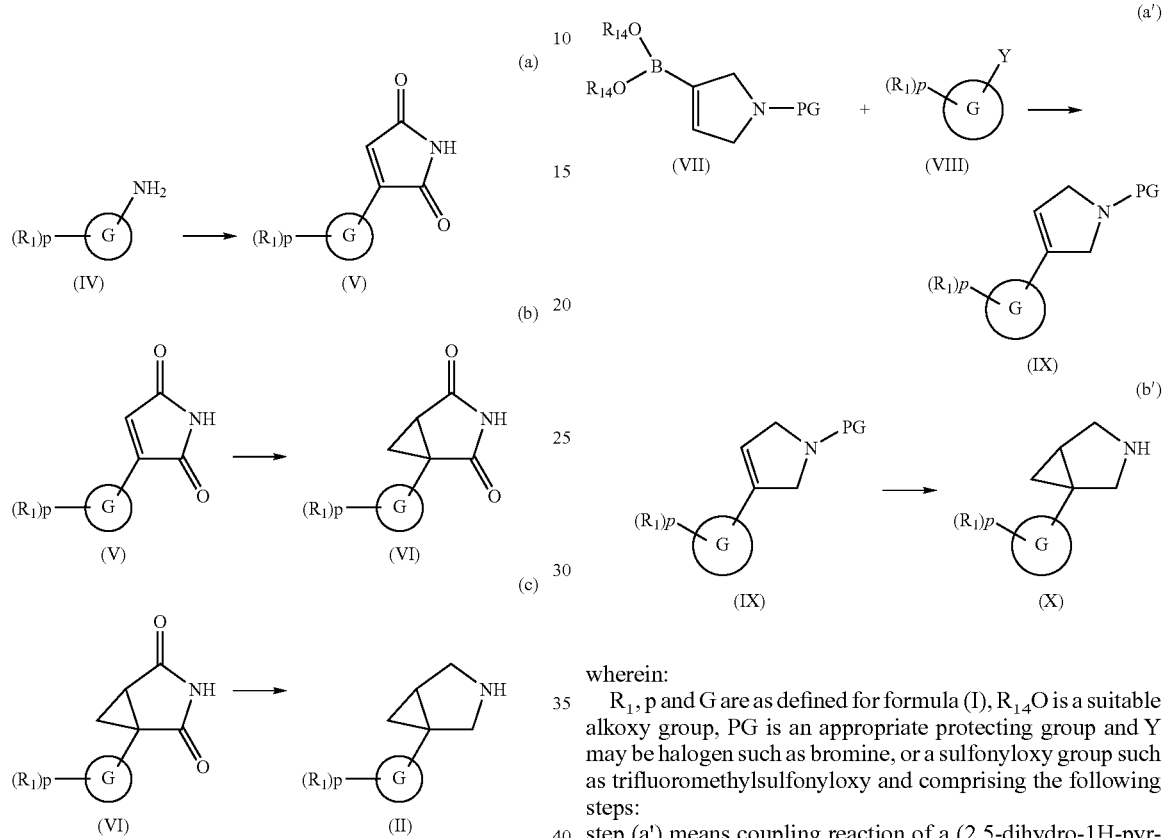

wherein step (a) means diazotation of an aniline (IV) followed by reaction with maleimide to give 3-arylmaleimide (V); step (b) means cyclopropanation of (V) to provide bicyclic imide (VI); and step (c) means reduction of imide (VI) to give compounds of formula (II).

Step (a) may be effected using conventional methods for the Meerwein reaction (e.g. *J. Am. Chem. Soc.* 1955, 77, 2313 describes the formation of arylmaleimides using this approach). Alternatively, in many cases this step is suitably performed applying a procedure where to a mixture of maleimide, an appropriate copper (II) salt such as anhydrous CuCl₂, and a suitable organonitrite, such as tert-butyl nitrite, in a compatible solvent, such as acetonitrile, is slowly added a solution of a compound of formula (IV). This is followed by allowing time to react as appropriate and a suitable workup.

Step (b) consists of slow addition of a solution of purified compound of formula (V), or mixtures containing a compound of formula (V), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (c) can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

An alternative synthetic process for the preparation of compounds of formula (II) is shown below:

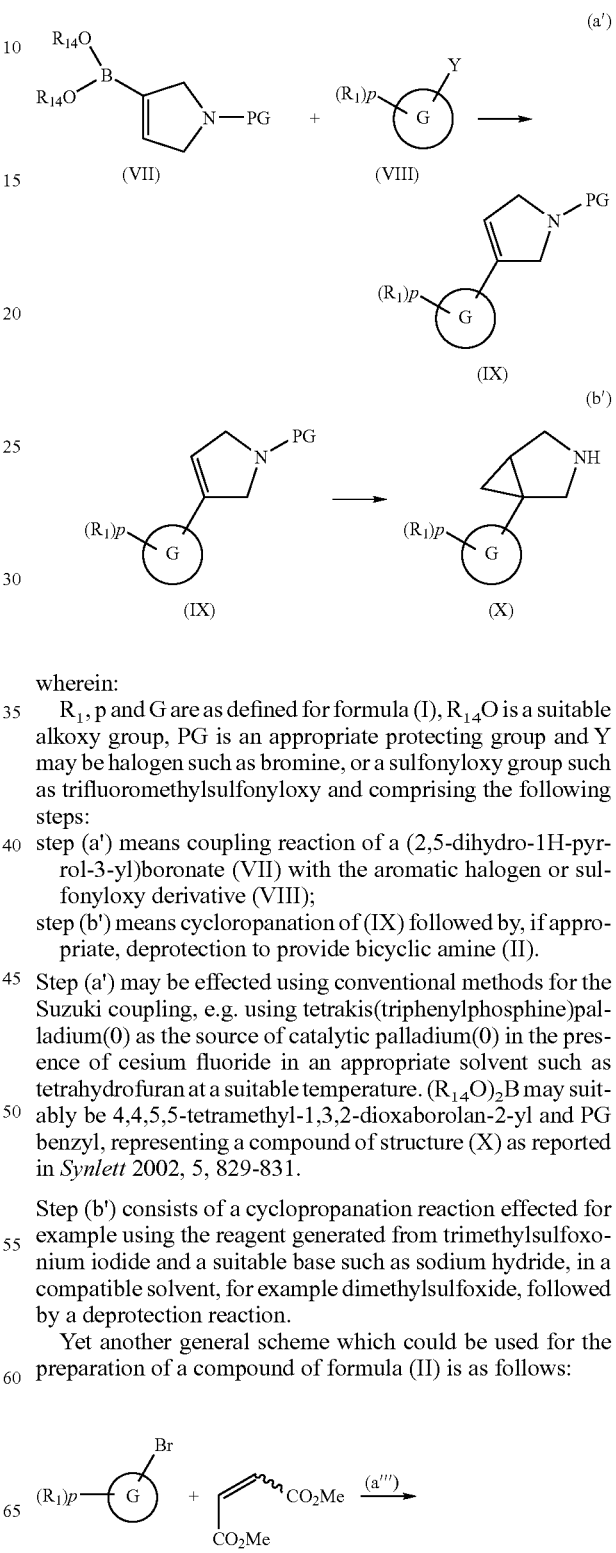

wherein:
R₁, p and G are as defined for formula (I), R₁₄O is a suitable alkoxy group, PG is an appropriate protecting group and Y may be halogen such as bromine, or a sulfonyloxy group such as trifluoromethylsulfonyloxy and comprising the following steps:
step (a') means coupling reaction of a (2,5-dihydro-1H-pyrrol-3-yl)boronate (VII) with the aromatic halogen or sulfonyloxy derivative (VIII);
step (b') means cyclopropanation of (IX) followed by, if appropriate, deprotection to provide bicyclic amine (II).

Step (a') may be effected using conventional methods for the Suzuki coupling, e.g. using tetrakis(triphenylphosphine)palladium(0) as the source of catalytic palladium(0) in the presence of cesium fluoride in an appropriate solvent such as tetrahydrofuran at a suitable temperature. (R₁₄O)₂B may suitably be 4,4,5,5-tetramethyl-1,3,2-dioxaborolan-2-yl and PG benzyl, representing a compound of structure (X) as reported in *Synlett* 2002, 5, 829-831.

Step (b') consists of a cyclopropanation reaction effected for example using the reagent generated from trimethylsulfoxonium iodide and a suitable base such as sodium hydride, in a compatible solvent, for example dimethylsulfoxide, followed by a deprotection reaction.

Yet another general scheme which could be used for the preparation of a compound of formula (II) is as follows:

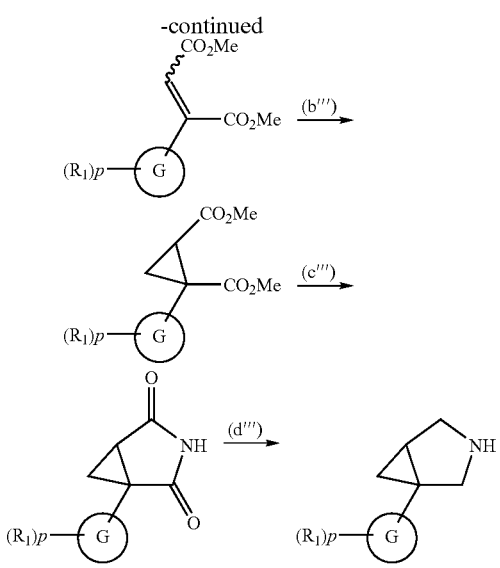

Step (a''') is a coupling reaction, mediated by for example palladium using diethyl maleate or fumarate as a common reagent (eg *Tetrahedron*, 2002, 58, 6545). Step (b''') is a cyclopropanation procedure, based on for example trimethylfulfoxonium iodide. Step (c''') is an ester hydrolysis step and a subsequent cyclization to imide, using for example urea. Finally, after step (d'''), a compound of formula (II) may be obtained following a vitride or borane based reduction procedure.

A compound of formula (III), wherein X is —S—, may itself be prepared by reacting a compound of formula (XII):

(XII)

wherein $R_3$ and $R_4$ are as hereinbefore defined; with a compound of formula (XIII):

L(CHR$_2$)(CH$_2$)$_2$Y  (XIII)

wherein $R_2$ is defined as for formula (I) and L and Y are leaving groups, e.g., a bromine or chlorine.

Interconversion reactions between compounds of formula (I) and salts thereof may be performed using methods well known in the art. Examples include:

(i) converting one or more of $R_1$ from alkoxy (e.g. methoxy) to hydroxy, (ii) converting one or more of $R_1$ from hydroxy to sulfonyloxy, such as alkylsulfonyloxy or haloalkylsulfonyloxy, e.g. methanesulfonyloxy or alkylsulfonyloxy or trifluoromethanesulfonyloxy, (iii) converting one or more of $R_1$ from halogen or perfluoroalkylsulfonyloxy to cyano; and optionally thereafter forming a salt of formula (I).

Compounds of formula (I) have been found to exhibit affinity for dopamine receptors, in particular the $D_3$ receptor, and are expected to be useful in the treatment of disease states which require modulation of such receptors, such as psychotic conditions. Such affinity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In the context of the present invention pKi (corresponding to the antilogarithm of Ki) is used instead of Ki and the compounds of the present invention typically show pKi greater than 6.5. In one aspect the present invention provides compounds of formula (I) having a pKi comprised between 6.5 and 8. In another aspect the present invention provides compounds of formula (I) having a pKi comprised between 8 and 9. In a further aspect the present invention provides compounds of formula (I) having a pKi greater than 9.

Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. $\geq 10\times$ or $\geq 100\times$ higher) affinity for dopamine $D_3$ than dopamine $D_2$ receptors (such affinity can be measured using standard methodology for example using cloned dopamine receptors—see herein). Said compounds may suitably be used as selective modulators of $D_3$ receptors.

From the localisation of $D_3$ receptors, it could also be envisaged that the compounds could also have utility for the treatment of a substance-related disorder where it has been suggested that $D_3$ receptors are involved (e.g. see Levant, 1997, Pharmacol. Rev., 49, 231-252). Examples of such substance abuse include alcohol, cocaine, heroin and nicotine abuse. Compounds of formula (I) may be used for treatment of all aspects of drug dependency including drug intake, relapse to drug-seeking behaviour following abstinence and withdrawal symptoms from drugs of abuse such as alcohol, cocaine, opiates, nicotine, benzodiazepines and inhibition of tolerance induced by opioids. In addition, compounds of formula (I) and salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242). Other conditions which may be treated by the compounds include dyskinetic disorders such as Parkinson's disease, neuroleptic-induced parkinsonism and tardive dyskinesias; depression; anxiety; cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

A wide range of psychiatric and neuropsychiatric disorders appear to be related to Obsessive-Compulsive Disorder, and form a family of related disorders referred to as obsessive-compulsive (OC) spectrum disorders. The compounds of formula (I) may be used for the treatment of an obsessive-compulsive spectrum disorder, including somatoform disorders such as body dysmorphic disorder and hyperchondriasis, bulimia nervosa, anorexia nervosa, binge eating, paraphilia and nonparaphilic sexual addictions, Sydeham's chorea, torticollis, autism, compulsive hoarding, and movement disorders, including Tourette's syndrome. As used herein, the phrase "obsessive-compulsive spectrum disorder" is intended to include Obsessive-Compulsive Disorder.

The compounds of formula (I) are also useful for the treatment of premature ejaculation.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "substance-related disorder" includes:—

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-induced Mood Disorder, Hallucinogen-induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Within the context of the present invention, the term "psychotic disorder" includes: —

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

In a further aspect therefore the present invention provides a method of treating a condition for which modulation [especially inhibition/antagonism (which may also translate into inverse agonism in constitutively active receptor systems)] of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof. In one embodiment, the condition is a substance-related disorder, a psychotic disorder or an obsessive compulsive spectrum disorder or premature ejaculation.

The invention also provides the use of a compound of formula (I) or a salt thereof in the manufacture of a medicament for the treatment of a condition in a mammal for which modulation (especially antagonism/inhibition) of dopamine receptors (especially dopamine $D_3$ receptors) is beneficial.

The invention also provides a compound of formula (I) or a salt thereof for use in the treatment of a condition in a mammal for which modulation [especially inhibition/antagonism (which may also translate into inverse agonism in constitutively active receptor systems)] of dopamine receptors (especially dopamine $D_3$ receptors) is beneficial.

In one embodiment, the compounds of the present invention are used in the treatment of a substance-related disorder, a psychotic disorder, an obsessive compulsive spectrum disorder or premature ejaculation.

Thus, a still further aspect the invention provides a method of treating a psychotic disorder (e.g. schizophrenia), a substance-related disorder, an obsessive compulsive spectrum disorder or premature ejaculation, which comprises administering to a mammal (e.g. human) in need thereof an effective amount of a compound of formula (I) as herein defined or a salt thereof.

Also provided is the use of a compound of formula (I) or a salt thereof in the manufacture of a medicament for the treatment of a psychotic disorder (e.g. schizophrenia), a substance-related disorder, an obsessive compulsive spectrum disorder or premature ejaculation.

Also provided is a compound of formula (I) or a salt thereof for use in the treatment of a psychotic disorder (e.g. schizophrenia), a substance-related disorder, an obsessive compulsive spectrum disorder or premature ejaculation.

Also provided is a compound of formula (I) or a salt thereof for use as a therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their salts which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a salt thereof calculated as the free base, the compound being administered 1 to 4 times per day. Suitably the compounds will be administered for a period of continuous therapy, for example for a week or more.

Biological Test Methods

Functional potency and intrinsic activity of compounds of this invention can be measured by the following GTPγS scintillation proximity assay (GTPγS-SPA). Cells used in the study are Chinese Hamster Ovary (CHO) Cells.

Cell Line

CHO_D2

CHO_D3

Compounds may be tested according to two alternative protocols:

a) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$2.12 \times 10^{-6}$ M Leupeptin (Sigma L2884)–5000× stock=5 mg/ml in buffer 25 ug/ml Bacitracin (Sigma B0125)–1000× stock=25 mg/ml in buffer 1 mM PMSF–100× stock=17 mg/ml in 100% ethanol $2 \times 10^{-6}$ M Pepstatin A–1000× stock=2 mM in 100% DMSO The cells are homogenised by 2×15 second bursts in a 1 litre Glass Waring blender in a class two biohazard cabinet. The resulting suspension is spun at 500 g for 20 mins (Beckman T21 centrifuge: 1550 rpm). The supernatant is withdrawn with a 25 ml pipette, aliquotted into pre-chilled centrifuge tubes and spun at 48,000 g to pellet membrane fragments (Beckman T1270: 23,000 rpm for 30 mins). The final 48,000 g pellet is resuspended in Homogenisation Buffer, (4× the volume of the original cell pellet). The 48,000 g pellet is resuspended by vortexing for 5 seconds and homogenized in a dounce homogenizer 10-15 stokes. The prep is distributed into appropriate sized aliquots, (200-1000 ul), in polypropylene tubes and store at –80° C. Protein content in the membrane preparations is evaluated with the Bradford protein assay.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 90 mins at 4° C.) membranes, 5 μg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM MgCl$_2$, 60 μg/ml saponin and 30 μM GDP is added. The third addition was a 20% TAV addition of either buffer, (agonist format) or EC$_{80}$ final assay concentration of agonist, Quinelorane, prepared in assay buffer (antagonist format). The assay was started by the addition of 29% TAV of GTPγ[$^{35}$S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 2-6 hours after the final addition.

The effect of the test drug over the basal generates EC$_{50}$ value by an iterative least squares curve fitting programme, expressed in the table as pEC$_{50}$ (i.e. –log EC$_{50}$). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the IC$_{50}$ generated by "antagonist format" experiment, using Cheng & Prusoff equation: fKi=IC$_{50}$/1+([A]/EC$_{50}$) where: [A] is the concentration of the agonist 5-HT in the assay and EC$_{50}$ is the 5-HT EC$_{50}$ value obtained in the same experiment. fpki is defined as –log fki.

b) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$10^{-4}$ M Leupeptin (Sigma L2884)

25 ug/ml Bacitracin (Sigma B0125)

1 mM PMSF–100× stock=17 mg/ml in 100% ethanol $2 \times 10^{-6}$ M Pepstatin A–500× stock=1 mM in 100% ethanol The cells were homgenised within a glass waring blender for 2×15 secs in 200 mls of 50 mM HEPES+10-4M leupeptin+25 ug/ml bacitracin+1 mM EDTA+1 mM PMSF+2 uM Pepstatin A, (the latter 2 reagents added as fresh ×100 and ×500 stocks respectively in ethanol). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and Pepstatin A. The material was then forced through a 0.6 mm needle, made up to the required volume, (usually ×4 the volume of the original cell pellet), aliquoted and stored frozen at –80 deg C.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 60 mins at RT) membranes, 5 μg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM MgCl2, 60 μg/ml saponin and 30 μM GDP is added. The third addition was a 20% TAV addition of either buffer, (agonist format) or EC80 final assay concentration of agonist, Quinelorane, prepared in assay buffer (antagonist format).

The assay was started by the addition of 29% TAV of GTP [35S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 3-6 hours after the final addition.

The effect of the test drug over the basal generates EC50 value by an iterative least squares curve fitting programme, expressed in the table as pEC50 (i.e. –log EC50). The ratio between the maximal effect of the test drug and the maximal effect of full agonist, Quinelorane, generates the Intrinsic Activity (IA) value (i.e. IA=1 full agonist, IA<1 partial agonist). fpki values of test drug are calculated from the $IC_{50}$ generated by "antagonist format" experiment, using Cheng & Prusoff equation: $fKi=IC_{50}/1+([A]/EC50)$ where: [A] is the concentration of the agonist Quinelorane in the assay and EC50 is the Quinelorane EC50 value obtained in the same experiment. fpKi is defined as –log fki. The compounds of the invention listed above have pKi values within the range of 6.5-10.5 at the dopamine D3 receptor. In one embodiment, compounds of the invention listed above have pKi values within the range of 7.0-10.5 at the dopamine D3 receptor. pKi results are only estimated to be accurate to about ±0.3-0.5.

The compounds of the invention listed above show selectivity over D2 receptor.

EXAMPLES

The invention is further illustrated by the following non-limiting examples.

All temperatures refer to ° C. Infrared spectra were measured on a FT-IR instrument. Compounds were analysed by direct infusion of the sample dissolved in acetonitrile into a mass spectra operated in positive electro spray (ES+) ionisation mode. Proton Magnetic Resonance ($^1$H-NMR) spectra were recorded at 400 MHz, chemical shifts are reported in ppm downfield (d) from $Me_4Si$, used as internal standard, and are assigned as singlets (s), broad singlets (bs), doublets (d), doublets of doublets (dd), triplets (t), quartets (q) or multiplets (m).

Column chromathography was carried out over silica gel (Merck A G Darmstaadt, Germany). The following abbreviations are used in the text: HOBt=1-hydroxybenzotriazole EtOAc=ethyl acetate, $Et_2O$=dietyl ether, DMF=N N'-dimethylformamide, MeOH=methanol, THF=tetrahydrofuran, DCC=1,3-dicyclohexyl-carbodiimide, SCX=strong cation exchanger, Tlc refers to thin layer chromatography on silica plates, and dried refers to a solution dried over anhydrous sodium sulphate, r.t. (RT) refers to room temperature, Rt=retention time, DMSO=dimethyl sulfoxide; AcOEt=ethyl acetate; DCM=dichloromethane; DCE=dichloroethane; EtOH=ethyl alcohol.

Preparation 1: diethyl-2-(2-methyl-6-quinolinyl)-2-butenedioate (P1)

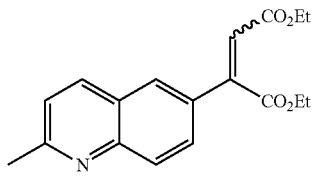

To a stirred solution of 6-bromo-2-methylquinoline (2.89 g) in DMF (70 mL) at room temperature, diethyl maleate (4.85 mL), palladium acetate (0.15 g), tri(o-tolyl)phosphine (0.39 g) and potassium carbonate (3.59 g) were subsequently added then the reaction mixture was warmed to 100° C. and stirring continued overnight. After cooling, the reaction mixture was quenched with water and extracted twice with diethyl ether. The combined organic layers were collected, dried over sodium sulphate and concentrated under reduced pressure. The crude product was purified by flash chromatography on silica gel (eluting with cyclohexane-ethyl acetate from 100 to 60%) to give 4 g of the title compound as a slightly yellow oil.

MS (m/z): 314 $[MH]^+$.

Preparation 2: diethyl 1-(2-methyl-6-quinolinyl)-1,2-cyclopropanedicarboxylate (P2)

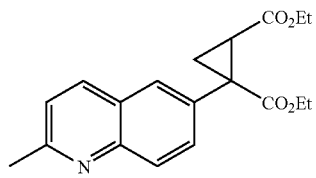

Sodium hydride (0.52 g) was added in small portions to a stirred suspension of trimethylsulfoxonium iodide (2.81 g) in DMSO (28 mL) at room temperature. After 0.5 h, the clear reaction mixture was cooled to 0° C. and a solution of diethyl-2-(2-methyl-6-quinolinyl)-2-butenedioate (2.0 g) in DMSO (14 mL) was quickly added and the stirring continued for 0.5 h after which time water (30 mL) was added. The mixture was extracted twice with ether (30 mL), the organic phase was washed with saturated ammonium chloride, dried over sodium sulphate and evaporated under reduced pressure to give 2 g of the title product which was used without further purification.

MS (m/z): 328 $[MH]^+$.

Preparation 3: (1R,5S/1S,5R)-1-(2-methyl-6-quinolinyl)-3-azabicyclo[3.1.0]hexane-2,4-dione (P3)

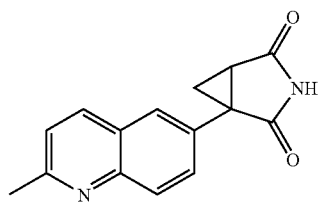

To a stirred solution of diethyl 1-(2-methyl-6-quinolinyl)-1,2-cyclopropanedicarboxylate (2 g) in THF (62 mL), at room temperature, lithium hydroxide (1.62 g) in water (13 mL) was added and the reaction mixture was warmed to 80° C. and stirred for 8 h. After cooling to room temperature, 6N hydrochloric acid was added up to pH 4-5 and the mixture concentrated under reduced pressure up to ⅓ of the initial volume. The aqueous solution was passed through a SCX cartridge (eluting with MeOH and 2N ammonia/MeOH), the organic phase was evaporated under reduced pressure and the residue was dried in oven to give the crude corresponding dicarboxylic acid intermediate (1.2 g). This material was suspended in xylene (30 mL), urea (0.53 g) was added and the reaction mixture was brought to reflux and stirred for 5 h. After cooling the reaction to room temperature, the mixture was extracted with 2% aqueous hydrochloric acid, the pH of the aqueous solution was brought approximately to 8-9 with sodium carbonate and the mixture was extracted with DCM. The organic phase was washed with water, dried over sodium sulphate and concentrated under reduce pressure to give the crude title product (0.66 g) which was used without further purification.

MS (m/z): 253 [MH]+.

Preparation 4: (1R,5S/1S,5R)-6-[3-azabicyclo[3.1.0]hex-1-yl]-2-methylquinoline (P4)

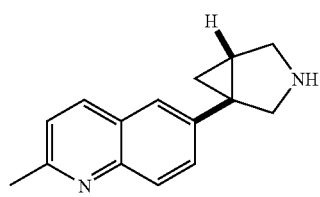

To a stirred solution of borane-THF complex (10.5 mL, 1M/THF) at 0° C., a solution of 1-(2-methyl-6-quinolinyl)-3-azabicyclo[3.1.0]hexane-2,4-dione (0.66 g) in THF (15 mL) was added dropwise then the reaction mixture was allowed to reach room temperature and refluxed for 5 h. The reaction mixture was then cooled to 0° C., and hydrochloric acid (20 mL, 6N) was added and the mixture stirred for 3 h at room temperature. Potassium carbonate was added up to pH about 9 then the mixture was extracted with DCM. The organic phase was washed with water, dried over sodium sulphate and concentrated under reduced pressure. The crude product was purified by flash chromatography (eluting with DCM/MeOH from 100 to 90%) to give the title compound (0.25 g) as a pale yellow foam.

NMR ($^1$H, DMSO): δ 9.5 (s, 1H), 9.4 (d, 1H), 7.98 (d, 1H), NH and NH2 not observed.

MS (m/z): 139 [MH]+.

Preparation 5: 3-[(3-chloropropyl)thio]-4-methyl-5-(4-methyl-1,3-oxazol-5-yl)-4H-1,2,4-triazole (P5)

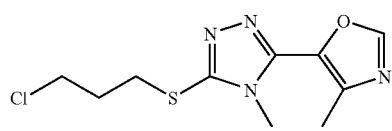

Ethyl-2-chloroacetoacetate (1 wt; 1 eq., 1000 g) was aged with formamide (0.68 vol; ca. 2.8 eq.) and the resulting solution was heated to 120° C. After 5 hours the mixture was allowed to cool to room temperature and allowed to age under nitrogen over night. The mixture was treated with NaOH (3 M, 6 vol, reaction moderately exothermic) and stirred at room temperature for 4 hours. Ethyl acetate (6 vol) was added and the phases allowed to separae. The organic layer was discarded while the aqueous was acidified with conc. (32%) aqueous HCl to pH 2 (ca. 2.0 vol). A precipitate started to form. The suspension was treated with AcOEt (8 vol) and vigorously stirred until the bulk of the precipitate had dissolved. The aqueous phase was further extracted with AcOEt twice (6 vol each) and the combined organic layers distilled to low volume (again a suspension was observed at low volume). Fresh AcOEt (8 vol) was added and the mixture evaporated to dryness. The collected solid was placed in the oven at 40° C. over night under reduced pressure to give 4-methyl-1,3-oxazole-5-carboxylic acid (498 g, 64.5%).

This material (498 g, 1 wt) was dissolved in dry tetrahydrofuran (5 vol), under nitrogen, cooled to 0° C. DCC (1.62 wt, 1 eq) was added portionwise followed by HOBt (1.07 wt, 1 eq). The mixture was warmed to 25±2° C. and stirred for 30 min. 4-Methyl-3-thiosemicarbazide (0.83 wt, 1 eq) was then added and the mixture further stirred for 2 h at 25±2° C. The mixture was filtered and the cake was washed with fresh tetrahydrofuran (1 vol) and dried on the filter for a few hours. The cake was suspended in 1 M aqueous NaOH (13 vol) and heated to 70° C. for 30 min. After this time, the mixture was cooled to 25±2° C. and a solid was removed by filtration. The cake was washed with 1 M aqueous NaOH (10 vol). The combined mother liquors were cooled to 0° C. and acidified to ca. pH 5 with HCl (aqueous, 16%; NOTE: keep temperature while adding HCl below +10° C.). The suspended product was isolated by filtration washing with water (2×3 vol). The cake was dried at 40° C. for 18 h in high vacuum to obtain 4-methyl-5-(4-methyl-1,3-oxazol-5-yl)-2,4-dihydro-3H-1,2,4-triazole-3-thione (respectively a tautomeric form thereof; 290 g, 37%).

NaOEt (21% solution in EtOH, 2.08 vol, 1.1 eq) was added to EtOH (20 vol) under nitrogen atmosphere. 4-Methyl-5-(4-methyl-1,3-oxazol-5-yl)-2,4-dihydro-3H-1,2,4-triazole-3-thione (respectively a tautomeric form thereof; 290 g, 1 wt) was added in one portion and the resulting mixture stirred at 25±2° C. until a clear solution was obtained. Then 1-bromo-3-chloropropane (0.54 vol, 1.1 eq) was added and the solution stirred at 40° C. for 24 h then cooled to 25° C. After filtration, water (20 vol) was added and the ethanolic phase removed by vacuum distillation (internal temperature ~40° C.). The mixture was extracted with EtOAc (41 vol). The aqueous layer was removed and the organic phase was evaporated to dryness. Dichloromethane (4 vol) was added. The organic solution is purified through a short silica gel column (18 wt of silica), eluting with EtOAc (200 vol) to give the title compound as a solid foam (267.64 g, 66%).

NMR ($^1$H, CDCl$_3$): δ 7.90 (s, 1H), 3.70 (s, 5H), 3.40 (t, 2H), 2.52 (s, 3H), 2.30 (m, 2H).

Preparation 6: 4-[(1R,5S/1S,5R)-3-(trifluoroacetyl)-3-azabicyclo[3.1.0]hex-1-yl]-phenol (P6)

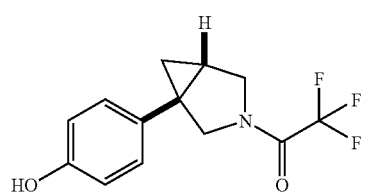

To a stirred solution of (1R,5S/1S,5R)-1-[4-(methyloxy)phenyl]-3-(trifluoroacetyl)-3-azabicyclo[3.1.0]hexane (0.6 g) in DCM (20 ml), at −78° C., tribromoborane (4.2 ml) was added dropwise over 5 minutes. The reaction was allowed to reach RT and stirring continued for 1 h, after which time aqueous saturated NaHCO₃ (15 ml) was added. Extraction with ethyl acetate of the reaction mixture provided after flash chromatography (eluting with cyclohexane:ethyl acetate from 10% to 60%) the title compound (0.54 g).

NMR ($^1$H, DMSO-D₆): δ 9.3 (bs, 1H), 7.1 (m, 2H), 6.65 (d, 2H), 4.1-3.55 (m, 4H), 1.95 (m, 1H), 1.0 (m, 1H), 0.65 (m, 1H).

Preparation 7: 2-nitro-4-[(1R,5S/1S,5R)-3-(trifluoroacetyl)-3-azabicyclo[3.1.0]hex-1-yl]phenol (P7)

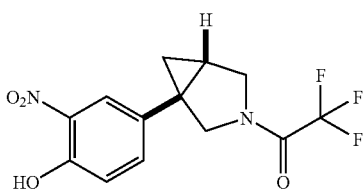

To a stirred solution of 4-[(1R,5S/1S,5R)-3-(trifluoroacetyl)-3-azabicyclo[3.1.0]hex-1-yl]phenol (0.14 g) in DCM (2 ml) at 0° C., dioxosilane (140 mg) and nitric acid (0.033 ml) were subsequently added. After 1.5 h, the reaction mixture was filtered through a celite panel, the filtered was washed with aqueous saturated NaHCO₃ (10 ml) and the solvent evaporated under vacuum to give the title compound (0.14 g) that was used without further purification.

NMR ($^1$H, DMSO-D₆): δ 7.8 (d, 1H), 7.45 (d, 1H), 7.0 (d, 1H), 4.1-3.6 (m, 4H), 2.05 (m, 1H), 1.1 (m, 1H), 0.75 (m, 1H), phenolic proton was not observed.

Preparation 8: 2-amino-4-[(1R,5S/1S,5R)-3-(trifluoroacetyl)-3-azabicyclo[3.1.0]hex-1-yl]phenol (P8)

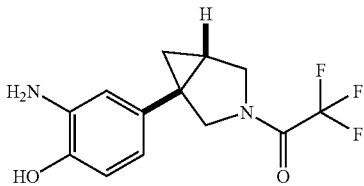

A stirred mixture of 2-nitro-4-[(1R,5S/1S,5R)-3-(trifluoroacetyl)-3-azabicyclo[3.1.0]hex-1-yl]phenol (0.24 g) and 10% palladium/C (0.048 g) in EtOH (10 ml) was hydrogenated (1 atm) for 3 h. Pd/C was filtered-off, the solid washed with EtOH (3×10 ml) and the filtered was evaporated under vacuum to give the title compound (0.22 g) which was used as such.

MS (m/z): 287 [MH]⁺.

Preparation 9: 5-[(1R,5S/1S,5R)-3-azabicyclo[3.1.0]hex-1-yl]-2-ethyl-1,3-benzoxazole (P9)

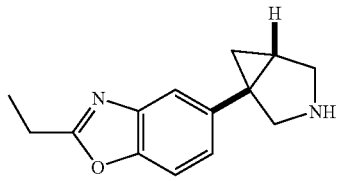

2-amino-4-[(1R,5S/1S,5R)-3-(trifluoroacetyl)-3-azabicyclo[3.1.0]hex-1-yl]phenol (0.11 g), 1,1,1-tris(ethyloxy)propane (0.216 ml) and 4-methylbenzenesulfonic acid (0.01 g) were added to DMF (1 ml) at RT. Reaction was stirred at 70° C. for 2 h than at 110° C. for further 2 h. Ethyl acetate was added and organic phase was washed with NaHCO₃ sat. Solvent was evaporated and residue dissolved in MeOH/H2O (1/1, 5 ml). Potassium carbonate was added (0.21 g) and reaction was heated at 60° C. After 2 h HF was added (4 ml) and reaction was heated at 60° C. for further 2 h. Water was added at RT, extraction with DCM provide after solvent removal title compound (0.19 g)

MS (m/z): 325.2 [MH]⁺.

Preparation 10: 3-(2-methyl-5-pyrimidinyl)-1H-pyrrole-2,5-dione (P10)

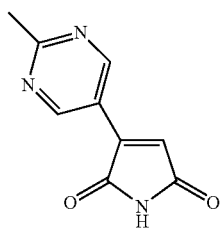

The title compound can be prepared by reacting 2-methyl-5-pyrimidinamine with maleimide in analogy with a conventional Meerwein reaction (J. Am. Chem. Soc. 1955, 77, 2313) or variations (e.g. J. Org. Chem., 1977, 42, 2431). To 2-methyl-5-pyrimidinamine (1 eq.) a solution of hydrochloric acid (37%, 2.6 eq.) and water should be added at room temperature with vigorous stirring and the formed precipitate should be allowed to stir for 30 minutes. Temperature should be reduced to 0° C. and sodium nitrite (1.1 eq.) in water added dropwise to the stirred suspension. At the end of diazotization, a clear solution should generally be obtained. Maleimide (2 eq.) in acetone should be added dropwise at 0° C. and then the pH of the solution adjusted to 3-3.5 by adding sodium acetate. Copper (II) chloride (0.15 eq.) should be added and vigorous stirring continued for 1 h at 0° C. then overnight at room temperature. Acetone should be removed in vacuo, the residue filtered and dried overnight in vacuo to give the title crude compound.

Preparation 11: (1R,5S/1S,5R)-1-(2-methyl-5-pyrimidinyl)-3-azabicyclo[3.1.0]hexane-2,4-dione (P11)

The title compound could be prepared following a cyclopropanation procedure based on trimethylsulfoxonium iodide. Milled sodium hydroxide (2 eq.) should be added in small portions to a stirred solution of trimethylsulfoxonium iodide (2 eq.) in DMSO. The resulting mixture should be allowed to stir at room temperature for 1.5 h then 3-(2-methyl-5-pyrimidinyl)-1H-pyrrole-2,5-dione (1 eq.) in DMSO added dropwise and the resulting mixture should be allowed to stir at room temperature for 20 minutes. Reaction temperature should be reduced to 0° C. and NH$_4$Cl (aqueous saturated solution) slowly added, followed by Et$_2$O. The organic phase should be washed with water, dried over Na$_2$SO$_4$ and evaporated to give the title crude product.

Preparation 12: (1R,5S/1S,5R)-1-(2-methyl-5-pyrimidinyl)-3-azabicyclo[3.1.0]hexane (P12)

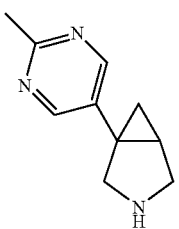

The title compound could be prepared following a normal reduction procedure from imide to amine. To a stirred solution of BH$_3$-THF complex (1M in tetrahydrofuran, 12 eq.), at 0° C., (1R,5S/1S,5R)-1-(2-methyl-5-pyrimidinyl)-3-azabicyclo[3.1.0]hexane-2,4-dione (1 eq.) in THF should be added dropwise. At the end of the addition the resulting mixture should be allowed to reach room temperature and refluxed for 4 hours. The mixture should be cooled to 0° C. then methanol and hydrochloric acid (6 M solution) added, followed by organic solvent removal under vacuum. A solution of sodium hydroxide (5 M) should be added until pH 9-10 is reached, the mixture extracted with Et$_2$O and the organic phase evaporated under vacuum to give the crude title product.

Preparation 13: (1-(Phenylmethyl)-3-(4,4,5,5-tetramethyl-1,3,2-dioxaborolan-2-yl)-2,5-dihydro-1H-pyrrole) (P13)

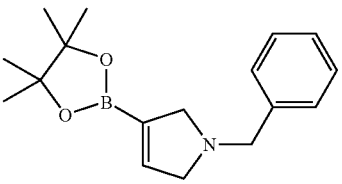

Diisopinocampheylborane was prepared following the procedure reported in *J. Org. Chem.* 1984, 49, 945-947. 2-[(1Z)-3-Chloro-1-(chloromethyl)-1-propen-1-yl]-4,4,5,5-tetramethyl-1,3,2-dioxaborolane (previously described in *Tetrahedron Lett.* 1993, 34, 4827-4828) was prepared following the general procedure reported in *Tetrahedron Lett.* 1989, 30, 2929, using 1,4-dichloro-2-butyne. The material thus obtained was further converted following the procedure reported in *Synlett* 2002, 5, 829-831. This latter procedure was modified in that isolation of the title product was achieved (rather than by distillation) by extraction of a solution of the crude reaction products in acetonitrile with cyclohexane, to provide the title compound (containing ~10% in moles of benzylamine) after evaporation of the volatiles from the cyclohexane phase.

Preparation 14: 2-methyl-5-[1-(phenylmethyl)-2,5-dihydro-1H-pyrrol-3-yl]pyrimidine (P14)

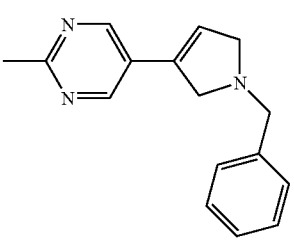

The title compound can be prepared through a coupling palladium mediated reaction, e.g. starting from 5-bromo-2-methylpyrimidine and 1-(phenylmethyl)-3-(4,4,5,5-tetramethyl-1,3,2-dioxaborolan-2-yl)-2,5-dihydro-1H-pyrrole. For example, to a solution of 5-bromo-2-methylpyrimidine (1.3 eq.) in THF, 1-(phenylmethyl)-3-(4,4,5,5-tetramethyl-1,3,2-dioxaborolan-2-yl)-2,5-dihydro-1H-pyrrole (1 eq.), tetrakis(triphenylphosphine)palladium(0) (5% mol) and cesium fluoride (4 eq.) may be added at room temperature. The resulting mixture should be stirred at 80° C. for 1.5 hours. After cooling the solvent should be evaporated under reduced pressure and the residue partitioned between dichloromethane and sodium hydroxyde (1M). The organic phase should be evaporated under reduced pressure and the crude product purified by flash chromatography to give the title compound.

Preparation 15: (1R,5S/1S,5R)-1-(2-methyl-5-pyrimidinyl)-3-(phenylmethyl)-3-azabicyclo[3.1.0]hexane (P15)

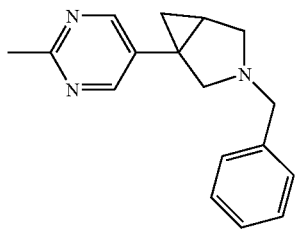

The title compound can be prepared following the procedure for the compound of Preparation 11.

Preparation 16: (1R,5S/1S,5R)-1-(2-methyl-5-pyrimidinyl)-3-azabicyclo[3.1.0]hexane (P16)

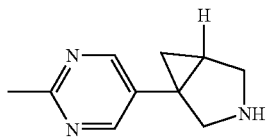

The title compound can be prepared following a normal hydrogenation reaction. A mixture of (1R,5S/1S,5R)-1-(2-methyl-5-pyrimidinyl)-3-(phenylmethyl)-3-azabicyclo[3.1.0]hexane (1 eq.), hydrochloridic acid, Pd/C, in ethanol may be hydrogenated at 1 atm up to starting material disappearance. The mixture should be filtered over celite and the organic phase evaporated under vacuum to give the crude title product.

Preparation 17: 3-(5-methyl-2-thienyl)-1-(phenylmethyl)-2,5-dihydro-1H-pyrrole (P17)

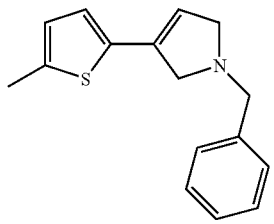

The title compound can be prepared through a coupling palladium mediated reaction, e.g. starting from 2-bromo-5-methylthiophene and 1-(phenylmethyl)-3-(4,4,5,5-tetramethyl-1,3,2-dioxaborolan-2-yl)-2,5-dihydro-1H-pyrrole. For example, to a solution of 2-bromo-5-methylthiophene (1.3 eq.) in THF, 1-(phenylmethyl)-3-(4,4,5,5-tetramethyl-1,3,2-dioxaborolan-2-yl)-2,5-dihydro-1H-pyrrole (1 eq.), tetrakis(triphenylphosphine)palladium(0) (5% mol) and cesium fluoride (4 eq.) may be added at room temperature. The resulting mixture should be stirred at 80° C. for 1.5 hours. After cooling the solvent should be evaporated under reduced pressure and the residue partitioned between dichloromethane and sodium hydroxyde (1M). The organic phase should be evaporated under reduced pressure and the crude product purified by flash chromatography to give the title compound.

Preparation 18: (1S,5S/1R,5R)-1-(5-methyl-2-thienyl)-3-(phenylmethyl)-3-azabicyclo[3.1.0]hexane (P18)

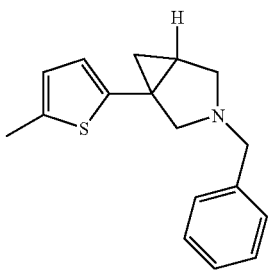

The title compound can be prepared following a zinc mediated cyclopropanation procedure (e.g Tetrahedron, 2003, 59, 6967). For example, 3-(5-methyl-2-thienyl)-1-(phenylmethyl)-2,5-dihydro-1H-pyrrole (1 eq.) in DCM may be added to a stirred mixture of diethylzinc (6 eq., 1M in hexanes) and diiodomethane (12 eq.) in DCM at 0° C. Quenching with NH$_4$Cl after disappearance of the starting material (monitored by MS) and purification of the crude product by flash chromatography should afford the title compound.

Preparation 19: (1S,5S/1R,5R)-1-(5-methyl-2-thienyl)-3-azabicyclo[3.1.0]hexane (P19)

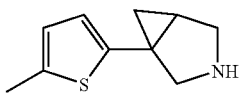

The title compound may be prepared following a benzyl removal, using for example an acyl chloride reagent (e.g.: J. Med. Chem., 1989, 32, 2534). A hydrogenation procedure is also possible. For example, to a solution of (1S,5S/1R,5R)-1-(5-methyl-2-thienyl)-3-(phenylmethyl)-3-azabicyclo[3.1.0]hexane (1 eq.) in 1,2-dichloroethane, at 0° C., 1-chloroethyl chloroformate (1.2 eq.) may be added. After refluxing the reaction mixture for the time needed (starting material disappearance as monitored by MS), the solvent should be removed under vacuum, methanol added and the mixture refluxed for 4 hours. Removal of the solvent, treatment of the residue with HCl (0.5 N) and following extraction of the mixture with ether after basification with NaOH should provide the crude title compound.

Preparation 20:
Diethyl-2-(6-quinoxalinyl)-2-butenedioate (P20)

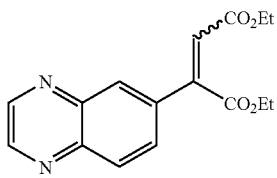

The title compound can be prepared through a palladium mediated coupling reaction, using diethyl maleate or fumarate as a common reagent (e.g. *Tetrahedron*, 2002, 58, 6545). For example, a mixture of 6-bromoquinoxaline (1 eq.), diethyl maleate (2.3 eq.), palladium acetate (0.05 eq.), tri(o-tolyl)phosphine (0.1 eq.) and potassium carbonate (2 eq.) in DMF may be warmed to 100° C. and stirred for 16 hours. Quenching with water, extraction with diethyl ether and purification of the crude product by flash chromatography should provide the title compound.

Preparation 21: diethyl-1-(6-quinoxalinyl)-1,2-cyclopropanedicarboxylate (P21)

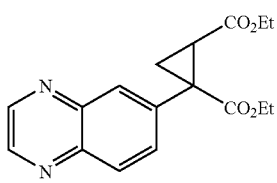

The title compound can be prepared through a cyclopropanation procedure based on trimethylsulfoxonium iodide. For example, milled sodium hydroxide (2 eq.) may be added in small portions to a stirred solution of trimethylsulfoxonium iodide (2 eq.) in DMSO. The resulting mixture may be allowed to stir at room temperature for 1.5 h then diethyl-2-(6-quinoxalinyl)-2-butenedioate (1 eq.) in DMSO may be added dropwise and the resulting mixture is allowed to stir at room temperature for 20 minutes. Reaction temperature should be reduced to 0° C. and $NH_4Cl$ (aqueous saturated solution) should be slowly added, followed by $Et_2O$. The organic phase may be washed with water, dried over $Na_2SO_4$ and evaporated to give the title crude product.

Preparation 22: (1R,5S/1S,5R)-1-(6-quinoxalinyl)-3-azabicyclo[3.1.0]hexane-2,4-dione (P22)

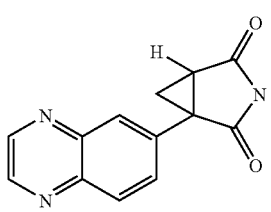

The title compound can be prepared following an ester hydrolysis to carboxylic acid and subsequent cyclization to imide using urea. For example, to a stirred solution of diethyl-1-(6-quinoxalinyl)-1,2-cyclopropanedicarboxylate (1 eq.) in THF, at room temperature, lithium hydroxide (2.5 eq.) in water may be added and the reaction mixture warmed to 80° C. and stirred for 8 h. After cooling to room temperature, 6N hydrochloric acid may be added up to pH 4-5 and the mixture concentrated under reduced pressure up to ⅓ of the initial volume. The aqueous solution may be passed through a SCX cartridge (eluting with MeOH and 2N ammonia/MeOH), the organic phase evaporated under reduced pressure and the residue dried in oven to give the crude corresponding dicarboxylic acid intermediate. This material should be suspended in xylene, urea (2 eq.) added and the reaction refluxed for 5 h. Following extraction with 2% aqueous hydrochloric acid, basification of the aqueous mixture and extraction with DCM should provide the title crude compound.

Preparation 23: (1R,5S/1S,5R)-6-[3-azabicyclo[3.1.0]hex-1-yl]quinoxaline (P23)

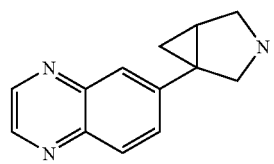

The title compound can be prepared following a vitride or borane based reduction procedure. For example, to a stirred solution of BH3-THF complex (1M in tetrahydrofuran, 12 eq.), at 0° C., (1R,5S/1S,5R)-1-(6-quinoxalinyl)-3-azabicyclo[3.1.0]hexane-2,4-dione (1 eq.) in THF may be added dropwise. At the end of the addition, the resulting mixture should be allowed to reach room temperature and refluxed for 4 hours. The mixture should be cooled to 0° C. then methanol and hydrochloric acid (6 M solution) added, followed by organic solvent removal under vacuum. A solution of sodium hydroxide (5 M) should be added until pH 9-10 is reached, the mixture extracted with $Et_2O$ and the organic phase evaporated under vacuum to give the crude title product.

Preparation 24:
diethyl-2-(5-quinolinyl)-2-butenedioate (P24)

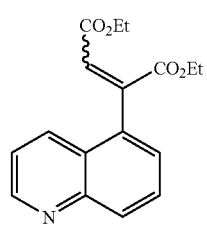

To a stirred solution of 5-bromo-2-methylquinoline (2.87 g) in DMF (60 mL) at room temperature, diethyl maleate (5.15 mL), palladium acetate (0.16 g), tri(o-tolyl)phosphine (0.42 g) and potassium carbonate (3.80 g) were subsequently added then the reaction mixture was warmed to 100° C. and stirring continued overnight. After cooling, the reaction mixture was quenched with water and extracted twice with diethyl ether. The combined organic layers were collected, dried over sodium sulphate and concentrated under reduced pressure. The crude product was purified by flash chromatography on silica gel (eluting with cyclohexane-ethyl acetate from 100 to 60%) to give 3.51 g of the title compound as a slightly yellow oil.

MS (m/z): 300 [MH]+.

Preparation 25: diethyl 1-(5-quinolinyl)-1,2-cyclopropanedicarboxylate (P25)

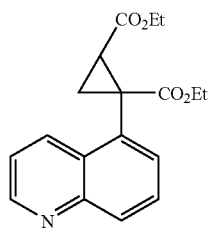

Sodium hydride (0.93 g) was added in small portions to a stirred suspension of trimethylsulfoxonium iodide (5.12 g) in DMSO (50 mL) at room temperature. After 0.5 h, the clear reaction mixture was cooled to 0° C. and a solution of diethyl-2-(5-quinolinyl)-2-butenedioate (P24, 3.48 g) in DMSO (25 mL) was quickly added and the stirring continued for 0.5 h after which time water (30 mL) was added. The mixture was extracted twice with ether (30 mL), the organic phase was washed with saturated ammonium chloride, dried over sodium sulphate and evaporated under reduced pressure. The crude product was purified by flash chromatography on silica gel (eluting with cyclohexane-ethyl acetate from 100 to 70%) to give 3.02 g of the title compound as a slightly yellow oil.

MS (m/z): 314 [MH]+.

Preparation 26: (1R,5S/1S,5R)-1-(5-quinolinyl)-3-azabicyclo[3.1.0]hexane-2,4-dione (P26)

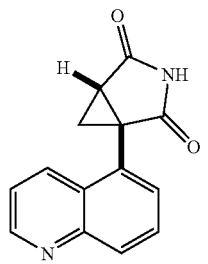

To a stirred solution of diethyl 1-(5-quinolinyl)-1,2-cyclopropanedicarboxylate (P25, 3.02 g) in THF (90 mL), at room temperature, lithium hydroxide (2.31 g) in water (23 mL) was added and the reaction mixture was warmed to 80° C. and stirred for 8 h. After cooling to room temperature, hydrochloric acid (37%) was added up to pH 4-5, the mixture partially concentrated under reduced pressure, extracted with DCM and the organic phase evaporated under reduced pressure to give a solid material that was dried in a vacuum oven at 100° C. overnight obtaining 1.7 g as a white solid.

A portion of this material (0.85 g) was suspended in xylene (65 mL), urea (1.0 g) was added and the reaction mixture was brought to reflux and stirred overnight. After cooling the reaction to room temperature, the mixture was extracted with 2% aqueous hydrochloric acid, the pH of the aqueous solution was brought approximately to 8 with NaHCO3 and the mixture was extracted with DCM. The organic solution was passed through a SCX cartridge (eluting with MeOH and 2N ammonia/MeOH) to give 120 mg of the crude title compound. This procedure was repeated for the remaining portion (85 mg). The two crude products were combined and purified by flash chromatography (eluting with DCM/MeOH from 100% to 96%) to give 165 mg of the title compound.

MS (m/z): 239 [MH]+.

Preparation 27: 5-[(1R,5S/1S,5R)-3-azabicyclo[3.1.0]hex-1-yl]quinoline (P27)

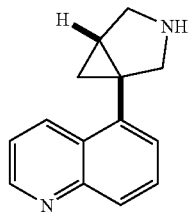

To a stirred solution of borane-THF complex (2.8 mL, 1M/THF) in THF (1 mL) at 0° C., a solution of 1-(2-methyl-6-quinolinyl)-3-azabicyclo[3.1.0]hexane-2,4-dione (P26, 165 mg) in THF (3 mL) was added dropwise then the reaction mixture was allowed to reach room temperature and refluxed for 3 h. The reaction mixture was then cooled to 0° C., hydrochloric acid (2N) was added and the mixture stirred for 3 h at room temperature. NaOH (1M) was added up to pH about 9, the mixture was extracted with DCM, the organic phase was washed with water, dried over sodium sulphate and concentrated under reduced pressure. The crude product was purified by flash chromatography (eluting with DCM/MeOH from 100 to 90%) to give the title compound (28 mg) as a pale yellow foam.

MS (m/z): 211 [MH]+.

Preparation 28: 2-[1-(phenylmethyl)-2,5-dihydro-1H-pyrrol-3-yl]pyrimidine (P28)

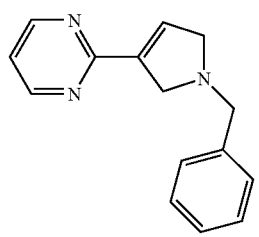

To a solution of 2-bromopyrimidine (0.88 g) in dry tetrahydrofuran (30 mL) 1-(phenylmethyl)-3-(4,4,5,5-tetramethyl- 1,3,2-dioxaborolan-2-yl)-2,5-dihydro-1H-pyrrole (P13, 1.21 g), tetrakis(triphenylphosphine)palladium(0) (0.25 g) and cesium fluoride (2.59 g) were added at room temperature. The resulting mixture was stirred at 80° C. for 6 hours. After cooling the solvent was evaporated under reduced pressure, the residue partitioned between ether and water and the organic phase was evaporated under reduced pressure. The crude product was purified by silica gel column chromatography (eluting with DCM/MeOH from 100% to 96%) to give 0.23 g of the title compound.

MS (m/z): 238 [MH]+.

Preparation 29: (1S,5S/1R,5R)-3-(phenylmethyl)-1-(2-pyrimidinyl)-3-azabicyclo[3.1.0]hexane (P29)

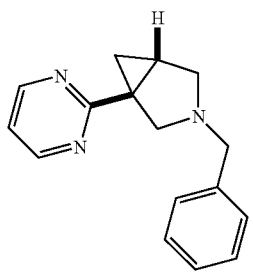

To a slurry of sodium hydride (80 mg) and trimethylsulfoxonium iodide (0.43 g) DMSO (anhydrous, 2.5 mL) was added dropwise (gas evolution) and the resulting mixture was allowed to stir at room temperature for 10 min then a solution of 2-[1-(phenylmethyl)-2,5-dihydro-1H-pyrrol-3-yl]pyrimidine (P28, 0.23 g) in DMSO (anhydrous, 1 mL) was added and the reaction mixture stirred for 0.5 h at 77° C. After cooling to room temperature water was added and the mixture extracted with ether twice, the organic phase was washed with brine, dried over sodium sulphate and evaporated under reduce pressure to give the crude title compound (0.15 g) that was used without further purification.

MS (m/z): 252 [MH]+.

Preparation 30: (1S,5S/1R,5R)-1-(2-pyrimidinyl)-3-azabicyclo[3.1.0]hexane (P30)

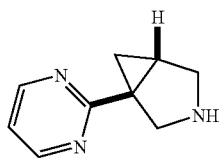

To a stirred solution of (1S,5S/1R,5R)-3-(phenylmethyl)-1-(2-pyrimidinyl)-3-azabicyclo[3.1.0]hexane (P29, 100 mg) in DCE (1 mL) at 0° C. and under a nitrogen atmosphere, 1-chloroethylchloroformate (0.052 mL) was added and after 10 min the reaction mixture was brought to reflux and stirred for 2.5 h. The reaction mixture was allowed to reach RT and the solvent evaporated under reduced pressure to give a crude product that was dissolved in methanol (4 mL), then the solution was refluxed for 2.5 h. The solvent was evaporated under reduced pressure and the residue was purified by flash chromatography (eluting with DCM/MeOH from 100% to 94%) to give the title compound (50 mg).

MS (m/z): 162 [MH]+.

Preparation 31: 3-[(3-chloropropyl)thio]-5-(3,4-difluorophenyl)-4-methyl-4H-1,2,4-triazole (P31)

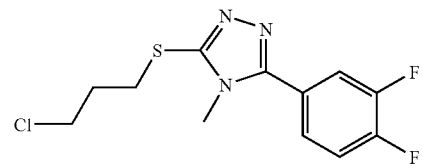

The title compound was prepared as reported in WO2005118549.

Example 1

2-methyl-6-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]quinoline hydrochloride (E1)

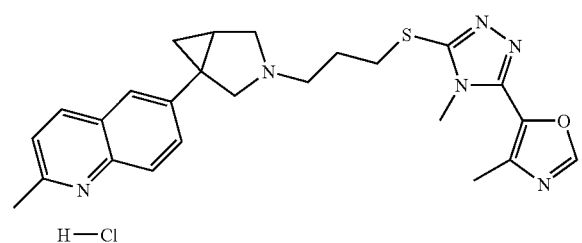

A mixture of (1R,5S/1S,5R)-6-[3-azabicyclo[3.1.0]hex-1-yl]-2-methylquinoline (150 mg), 3-[(3-chloropropyl)thio]-4-methyl-5-(4-methyl-1,3-oxazol-5-yl)-4H-1,2,4-triazole (236 mg), potassium carbonate (110 mg) and sodium iodide (119 mg) in anhydrous DMF (3 mL) was heated at 60° C. for 24 h. After elimination of the solvent in vacuo the residue was dissolved in ethyl acetate (10 mL) and the organic phase was washed with water, dried over sodium sulphate and concentrated in vacuo. The crude was purified by flash chromatography on silica gel (dichloromethane to 10% MeOH in dichloromethane) to give 150 mg of the free base of the title compound. To a solution of this material in dichloromethane (2 mL) was added HCl (0.13 mL, 1 M in Et$_2$O), the solvent evaporated under vacuo and the material thus obtained triturated with Et$_2$O to give 136 mg of the title compound as a pale yellow solid.

NMR ($^1$H, CDCl$_3$): 10.36 (bs, 1H), 8.57 (s, 1H), 8.28 (m, 1H), 7.94 (m, 1H), 7.87 (m, 1H), 7.66 (m, 1H), 7.49 (m, 1H), 4.11 (m, 1H), 3.75 (m, 2H), 3.69 (s, 3H), 3.56 (m, 1H), 3:31 (m, 4H), 2.69 (s, 3H), 2.37 (s, 3H), 2.31 (m, 1H), 2.18 (m, 2H), 1.67 (m, 1H), 1.26 (m, 1H).

MS (m/z): 461 [MH]+.

Example 2

2-ethyl-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzoxazole hydrochloride (E2)

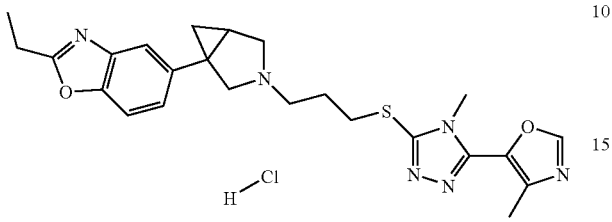

A mixture of 5-[(1R,5S/1S,5R)-3-azabicyclo[3.1.0]hex-1-yl]-2-ethyl-1,3-benzoxazole (50 mg) and 3-[(3-chloropropyl)thio]-4-methyl-5-(4-methyl-1,3-oxazol-5-yl)-4H-1,2,4-triazole (60 mg), potassium carbonate (35 mg) and sodium iodide (33 mg) in anhydrous DMF (0.2 mL) was heated at 60° C. for 24 h. After elimination of the solvent in vacuo the residue was dissolved in ethyl acetate (5 mL) and the organic phase was washed with water, dried over sodium sulphate and concentrated in vacuo. The crude was purified by flash chromatography on silica gel (dichloromethane to 10% MeOH in dichloromethane) to give 150 mg of the free base of the title compound. To a solution of this material in dichloromethane (2 mL) was added HCl (0.22 mL, 1 M in $Et_2O$), the solvent evaporated under vacuo and the material thus obtained triturated with $Et_2O$ to give 12 mg of the title compound as a white hygroscopic solid.

NMR ($^1$H, $CD_3OD$): METHANOL-$d_4$ δ ppm 8.41 (s, 1H), 7.67 (d, 1H), 7.59 (d, 1H), 7.40 (dd, 1H), 4.17 (d, 1H), 3.91 (d, 1H), 3.81 (s, 3H), 3.73 (dd, 1H), 3.67 (d, 1H), 3.48-3.55 (m, 2H), 3.43 (t, 2H), 3.02 (q, 2H), 2.47 (s, 3H), 2.25-2.34 (m, 3H), 1.48-1.54 (m, 1H), 1.45 (t, 3H), 1.35-1.41 (m, 1H), hydrochloridric proton was not observed. MS (m/z): 465.5 [MH]$^+$.

Example 3

(1R,5S/1S,5R)-6-[3-(3-{[4-methyl-5-(4-methyl-1,3-oxazol-5-yl)-4H-1,2,4-triazol-3-yl]thio}propyl)-3-azabicyclo[3.1.0]hex-1-yl]quinoxaline hydrochloride (E3)

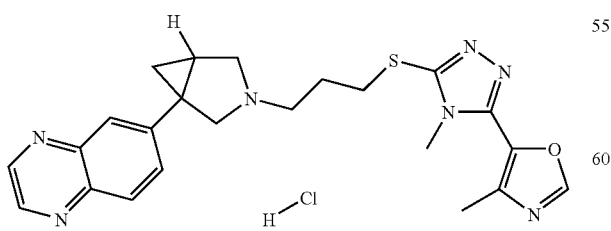

It is believed that the title compound may be prepared using (1R,5S/1S,5R)-6-[3-azabicyclo[3.1.0]hex-1-yl]quinoxaline and 3-[(3-chloropropyl)thio]-4-methyl-5-(4-methyl-1,3-oxazol-5-yl)-4H-1,2,4-triazole, using similar methods to the preparation of Examples 1 and 2.

Example 4

(1R,5S/1S,5R)-3-(3-{[4-methyl-5-(4-methyl-1,3-oxazol-5-yl)-4H-1,2,4-triazol-3-yl]thio}propyl)-1-(2-methyl-5-pyrimidinyl)-3-azabicyclo[3.1.0]hexane hydrochloride (E4)

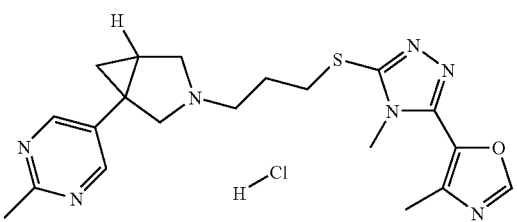

It is believed that the title compound may be prepared using (1R,5S/1S,5R)-1-(2-methyl-5-pyrimidinyl)-3-azabicyclo[3.1.0]hexane and 3-[(3-chloropropyl)thio]-4-methyl-5-(4-methyl-1,3-oxazol-5-yl)-4H-1,2,4-triazole, using similar methods to the preparation of Examples 1 and 2.

Example 5

(1S,5S/1R,5R)-3-(3-{[4-methyl-5-(4-methyl-1,3-oxazol-5-yl)-4H-1,2,4-triazol-3-yl]thio}propyl)-1-(5-methyl-2-thienyl)-3-azabicyclo[3.1.0]hexane hydrochloride (E5)

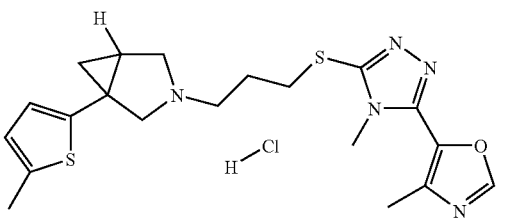

It is believed that the title compound may be prepared using (1S,5S/1R,5R)-1-(5-methyl-2-thienyl)-3-azabicyclo[3.1.0]hexane and 3-[(3-chloropropyl)thio]-4-methyl-5-(4-methyl-1,3-oxazol-5-yl)-4H-1,2,4-triazole, using similar methods to the preparation of Examples 1 and 2.

Example 6

5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]quinoline hydrochloride (E6)

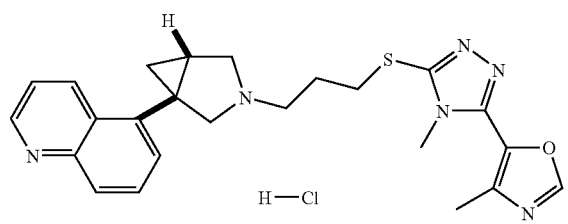

A mixture of 5-[(1R,5S/1S,5R)-3-azabicyclo[3.1.0]hex-1-yl]quinoline (P27, 28 mg), 3-[(3-chloropropyl)thio]-4-methyl-5-(4-methyl-1,3-oxazol-5-yl)-4H-1,2,4-triazole (P5, 47 mg), K$_2$CO$_3$ (22 mg) and NaI (24 mg) in DMF (anhydrous, 0.6 mL) was heated at 60° C. for 24 h. After elimination of the solvent under reduced pressure the residue was dissolved in ethyl acetate, the organic layer was washed with water and dried over Na$_2$SO$_4$ and the solvent evaporated under reduced pressure. The crude was purified by flash chromatography (eluting with DCM/MeOH from 100% to 96%) to give 18 mg of the free base of the title compound. To a solution of this material in dichloromethane (0.2 mL) was added HCl (1M in Et$_2$O, 0.038 mL), the solvent evaporated in vacuo and the material thus obtained triturated with Et$_2$O to give 18 mg of the title compound as a white slightly hygroscopic solid.

$^1$H NMR (400 MHz, DMSO-d$_6$) δ ppm 10.21-10.40 (br. s., 1H) 8.85-9.00 (m, 1H) 8.54-8.65 (m, 1H) 8.46-8.55 (m, 1H) 7.90-8.06 (m, 1H) 7.68-7.80 (m, 2H) 7.53-7.67 (m, 1H) 4.02-4.16 (m, 1H) 3.72-3.89 (m, 2H) 3.58-3.66 (m, 4H) 3.16-3.27 (m, 4H) 2.28-2.36 (m, 3H) 2.19-2.27 (m, 1H) 2.02-2.17 (m, 2H) 1.70-1.79 (m, 1H) 1.00-1.08 (m, 1H); MS (m/z): 447 [MH]$^+$.

Example 7

(1S,5S/1R,5R)-3-(3-{[4-methyl-5-(4-methyl-1,3-oxazol-5-yl)-4H-1,2,4-triazol-3-yl]thio}propyl)-1-(2-pyrimidinyl)-3-azabicyclo[3.1.0]hexane hydrochloride (E7)

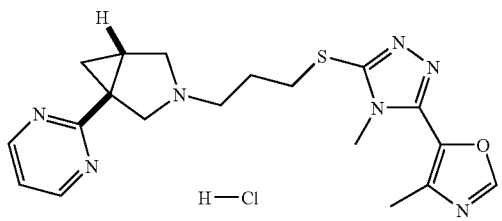

A mixture of (1S,5S/1R,5R)-1-(2-pyrimidinyl)-3-azabicyclo[3.1.0]hexane (P30, 25 mg), 3-[(3-chloropropyl)thio]-4-methyl-5-(4-methyl-1,3-oxazol-5-yl)-4H-1,2,4-triazole (P5, 55 mg), K$_2$CO$_3$ (28 mg) and NaI (27 mg) in DMF (anhydrous, 0.5 mL) was heated at 60° C. for 24 h. After elimination of the solvent under reduced pressure the residue was dissolved in ethyl acetate, the organic layer was washed with water and dried over Na$_2$SO$_4$ and the solvent evaporated under reduced pressure. The crude was purified by flash chromatography (eluting with DCM/MeOH from 100% to 90%) to give 21 mg of the free base of the title compound. To a solution of this material in dichloromethane (0.5 mL) was added HCl (1M in Et$_2$O, 0.052 mL), the solvent evaporated in vacuo and the material thus obtained triturated with Et$_2$O to give 21 mg of the title compound as a white slightly hygroscopic solid.

$^1$H NMR (500 MHz, DMSO-d$_6$) δ ppm 10.38 (br. s., 1H) 8.73 (d, 2H) 8.55-8.59 (m, 1H) 7.38 (d, 1H) 3.92-4.03 (m, 2H) 3.70-3.76 (m, 1H) 3.66-3.70 (m, 3H) 3.47-3.54 (m, 1H) 3.32-3.44 (m, 2H) 3.26 (t, 2H) 2.34-2.40 (m, 2H) 2.27-2.33 (m, 1H) 2.11-2.22 (m, 2H) 1.74-1.83 (m, 1H) 1.57-1.65 (m, 1H); MS 398 (m/z): [MH]$^+$.

Example 8

(1S,5S/1R,5R)-3-(3-{[5-(3,4-difluorophenyl)-4-methyl-4H-1,2,4-triazol-3-yl]thio}propyl)-1-(2-pyrimidinyl)-3-azabicyclo[3.1.0]hexane hydrochloride (E8)

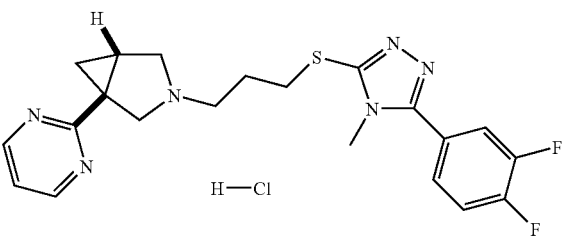

A mixture of (1S,5S/1R,5R)-1-(2-pyrimidinyl)-3-azabicyclo[3.1.0]hexane (P30, 25 mg), 3-[(3-chloropropyl)thio]-5-(3,4-difluorophenyl)-4-methyl-4H-1,2,4-triazole (P31, 55 mg), K$_2$CO$_3$ (28 mg) and NaI (27 mg) in DMF (anhydrous, 0.5 mL) was heated at 60° C. for 24 h. After elimination of the solvent under reduced pressure the residue was dissolved in ethyl acetate, the organic layer was washed with water and dried over Na$_2$SO$_4$ and the solvent evaporated under reduced pressure. The crude was purified by flash chromatography (eluting with DCM/MeOH from 100% to 90%) to give 21 mg of the free base of the title compound. To a solution of this material in dichloromethane (0.5 mL) was added HCl (1M in Et$_2$O, 0.052 mL), the solvent evaporated in vacuo and the material thus obtained triturated with Et$_2$O to give 21 mg of the title compound as a white slightly hygroscopic solid.

$^1$H NMR (500 MHz, DMSO-d$_6$) δ ppm 10.44-10.57 (br. s., 1H) 8.68-8.77 (m, 2H) 7.80-7.89 (m, 1H) 7.62-7.71 (m, 1H) 7.57-7.62 (m, 1H) 7.34-7.42 (m, 1H) 3.92-4.05 (m, 2H) 3.67-3.77 (m, 1H) 3.58-3.64 (m, 3H) 3.19-3.41 (m, 5H) 2.27-2.34 (m, 1H) 2.09-2.23 (m, 2H) 1.77-1.87 (m, 1H) 1.55-1.65 (m, 1H);
MS 429 (m/z): [MH]$^+$.

All publications, including but not limited to patents and patent applications, cited in this specification are herein incorporated by reference as if each individual publication were specifically and individually indicated to be incorporated by reference herein as though fully set forth.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (I) or a salt thereof:

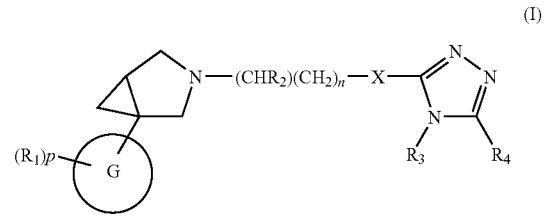

wherein:
G is a 5- or 6-membered heteroaromatic group, or is a 9- or 10-membered bicyclic heteroaromatic group containing one or two heteroatoms independently selected from the group consisting of nitrogen and oxygen, with the proviso that G is not pyridyl, indazolyl or benzothiazolyl;

p is 0 to 4;

$R_1$ is independently selected from the group consisting of halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or is $R_5$;

$R_2$ is hydrogen or $C_{1-4}$alkyl;

n is 2 or 3;

X is S or —$CH_2$—;

$R_3$ is $C_{1-4}$alkyl;

$R_4$ is hydrogen, phenyl, heterocyclyl, a 5- or 6-membered heteroaromatic group, or a 8- to 11-membered bicyclic group, any of which groups is optionally substituted by 1, 2, 3 or 4 substituents selected from the group consisting of halogen, cyano, $C_{1-4}$alkyl, halo$C_{1-4}$alkyl, $C_{1-4}$alkoxy and $C_{1-4}$-alkanoyl; and $R_5$ is isoxazolyl, —$CH_2$—N-pyrrolyl, 1,1-dioxido-2-isothiazolidinyl, thienyl, thiazolyl, pyridyl or 2-pyrrolidinonyl, wherein each group is optionally substituted by one or two substituents selected from: halogen, cyano, $C_{1-4}$alkyl, halo$C_{1-4}$alkyl, $C_{1-4}$alkoxy and $C_{1-4}$alkanoyl.

2. A compound as claimed in claim 1, wherein G is quinolinyl, benzoxazolyl or pyrimidyl.

3. A compound as claimed in claim 1, wherein $R_1$ is $C_{1-4}$alkyl.

4. A compound as claimed in claim 1, wherein $R_2$ is hydrogen and n is 1.

5. A compound as claimed in claim 1, wherein X is —S—.

6. A compound as claimed in claim 1, wherein $R_4$ is optionally substituted phenyl (e.g. phenyl, 4-trifluoromethyl-phenyl, 3,4-difluorophenyl) or optionally substituted oxazolyl (e.g. 4-methyl-1,3-oxazol-5-yl, 2-methyl-5-trifluoromethyl-1,3-oxazol-4-yl).

7. A compound as claimed in claim 1 wherein $R_4$ is phenyl, 4-trifluoromethyl-phenyl, 3,4-difluorophenyl, 4-methyl-1,3-oxazol-5-yl, or 2-methyl-5-trifluoromethyl-1,3-oxazol-4-yl.

8. A compound as claimed in claim 1, wherein $R_3$ is methyl.

9. A compound as claimed in claim 1, having a formula (I)' or a salt thereof

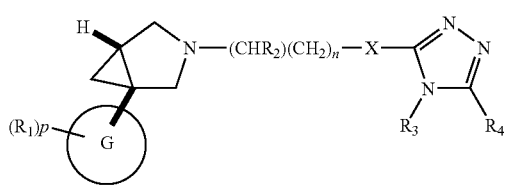

(I)' wherein G, p, $R_1$, $R_2$, $R_3$ and $R_4$ are defined as in claim 1 for compounds of formula (I).

10. A compound as claimed in claim 1 having a formula (IC) or a salt thereof, wherein $R_1$, p, $R_3$ and $R_4$ are as defined claim 1:

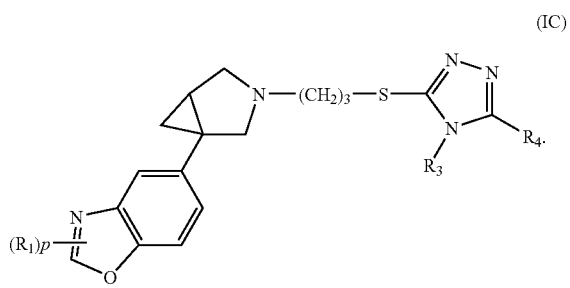

(IC)

11. A compound as claimed in claim 1 having a formula (ID) or a salt thereof, wherein $R_1$, p, $R_3$ and $R_4$ are as defined in claim 1:

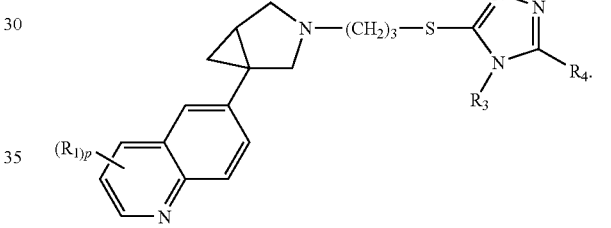

(ID)

12. A compound as claimed in claim 11 having a formula (IE) or a salt thereof, wherein $R_1$, p, $R_3$ and $R_4$ are as defined in claim 1:

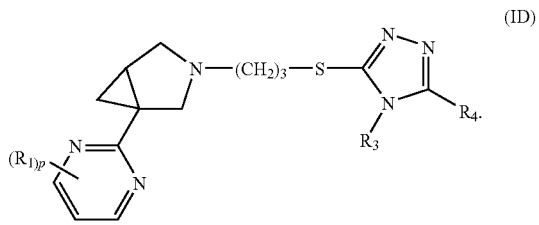

(ID)

13. A compound as claimed in claim 1, which is
2-methyl-6-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]quinoline;
2-ethyl-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzoxazole;

5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]quinoline;

(1S,5S/1R,5R)-3-(3-{[4-methyl-5-(4-methyl-1,3-oxazol-5-yl)-4H-1,2,4-triazol-3-yl]thio}propyl)-1-(2-pyrimidinyl)-3-azabicyclo[3.1.0]hexane;

(1S,5S/1R,5R)-3-(3-{[5-(3,4-difluorophenyl)-4-methyl-4H-1,2,4-triazol-3-yl]thio}propyl)-1-(2-pyrimidinyl)-3-azabicyclo[3.1.0]hexane;

or a salt thereof.

14. A process for preparing a compound as defined in claim 1, which process comprises reacting a compound of formula (II):

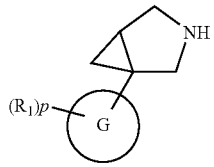

wherein $R_1$, p and G are as defined for formula (I), with a compound of formula (III):

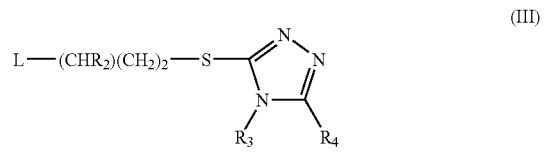

wherein $R_2$, $R_3$ and $R_4$ are as defined for formula (I) and L is a leaving group, and thereafter optionally:
(i) removing any protecting group(s); and/or
(ii) forming a salt; and/or
(iii) converting a compound of formula (I) or a salt thereof to another compound of formula (I) or a salt thereof.

15. A pharmaceutical composition comprising a compound as claimed in claim 1 and a pharmaceutically acceptable carrier.

* * * * *